(12) United States Patent
Lee et al.

(10) Patent No.: US 12,121,084 B2
(45) Date of Patent: Oct. 22, 2024

(54) MASK DEVICE AND METHOD FOR CONTROLLING THE SAME

(71) Applicant: LG ELECTRONICS INC., Seoul (KR)

(72) Inventors: Keonwang Lee, Seoul (KR); Seongman Jang, Seoul (KR); Hyungho Park, Seoul (KR); Hoojin Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 639 days.

(21) Appl. No.: 17/599,507

(22) PCT Filed: Jan. 20, 2020

(86) PCT No.: PCT/KR2020/000912
§ 371 (c)(1),
(2) Date: Sep. 28, 2021

(87) PCT Pub. No.: WO2020/204320
PCT Pub. Date: Oct. 8, 2020

(65) Prior Publication Data
US 2022/0192289 A1    Jun. 23, 2022

(30) Foreign Application Priority Data

Mar. 29, 2019 (KR) .................. 10-2019-0037323

(51) Int. Cl.
| | | |
|---|---|---|
| *A41D 13/11* | (2006.01) | |
| *A61B 5/087* | (2006.01) | |
| *A61B 5/11* | (2006.01) | |
| *A62B 18/00* | (2006.01) | |
| *A62B 18/02* | (2006.01) | |
| *A62B 18/08* | (2006.01) | |

(Continued)

(52) U.S. Cl.
CPC ...... *A41D 13/1107* (2013.01); *A41D 13/1161* (2013.01); *A61B 5/087* (2013.01);
(Continued)

(58) Field of Classification Search
CPC .......... A62B 18/00–10; A62B 9/00–06; A62B 7/00–14; A62B 23/00–025;
(Continued)

(56) References Cited

U.S. PATENT DOCUMENTS 5,303,701 A * 4/1994 Heins .................. A62B 18/006
128/204.22
2008/0127979 A1* 6/2008 Becker ................ A62B 18/006
128/205.27

(Continued)

FOREIGN PATENT DOCUMENTS

CN    204182039 U    3/2015
CN    104548406 A    4/2015
(Continued)

*Primary Examiner* — Rachel T Sippel
*Assistant Examiner* — Jacqueline M Pinderski
(74) *Attorney, Agent, or Firm* — Bryan Cave Leighton Paisner LLP

(57) ABSTRACT

Provided are a mask device and a method for controlling the same. The mask device includes a mask body configured to cover a nose and mouth of a user, a first air cleaner connected to one side of the mask body, and a second air cleaner connected to the other side of the mask body. Also, the mask device includes a first suction fan module installed in the first air cleaner, a second suction fan module installed in the second air cleaner, and an exhaust fan module disposed in the mask body.

18 Claims, 14 Drawing Sheets

(51) Int. Cl.
*A62B 23/02* (2006.01)
*F04D 19/00* (2006.01)
*F04D 27/00* (2006.01)
*F04D 29/70* (2006.01)

(52) U.S. Cl.
CPC .......... *A61B 5/1118* (2013.01); *A62B 18/006* (2013.01); *A62B 18/025* (2013.01); *A62B 18/086* (2013.01); *A62B 23/02* (2013.01); *F04D 19/002* (2013.01); *F04D 27/004* (2013.01); *F04D 27/007* (2013.01); *F04D 27/008* (2013.01); *F04D 29/703* (2013.01)

(58) Field of Classification Search
CPC ............ A41D 13/1107; A41D 13/1161; A61B 5/087–09; A61B 5/1118; F04D 19/002; F04D 27/004; F04D 27/007; F04D 27/008; F04D 29/703; F04D 25/084; F04D 25/08; F04D 25/166
See application file for complete search history.

(56) References Cited

U.S. PATENT DOCUMENTS

| | | |
|---|---|---|
| 2009/0217926 A1 | 9/2009 | Hine et al. |
| 2009/0266361 A1 | 10/2009 | Bilger et al. |
| 2013/0319408 A1 | 12/2013 | Zwolinsky et al. |
| 2015/0136142 A1 | 5/2015 | Blomberg |
| 2015/0202473 A1* | 7/2015 | Curran .................. A62B 23/025 128/205.27 |
| 2018/0185677 A1 | 7/2018 | Curran et al. |
| 2019/0009114 A1 | 1/2019 | Han |

FOREIGN PATENT DOCUMENTS

| | | |
|---|---|---|
| CN | 105876933 A | 8/2016 |
| CN | 206285364 U | 6/2017 |
| CN | 107149182 A | 9/2017 |
| CN | 107822232 A | 3/2018 |
| CN | 207076032 U | 3/2018 |
| CN | 107929969 A | 4/2018 |
| CN | 108367181 A | 8/2018 |
| CN | 108371361 A | 8/2018 |
| CN | 108939337 A | 12/2018 |
| CN | 208403333 U | 1/2019 |
| EP | 3446756 A1 | 2/2019 |
| JP | 201687376 A | 5/2016 |
| KR | 200422942 Y1 | 8/2006 |
| KR | 10-2016-0086893 A | 7/2016 |
| KR | 10-1783804 B1 | 10/2017 |
| KR | 1020170111132 A | 10/2017 |
| WO | 2011051715 A2 | 5/2011 |
| WO | 2019-016018 A1 | 1/2019 |

* cited by examiner

【Figure 1】
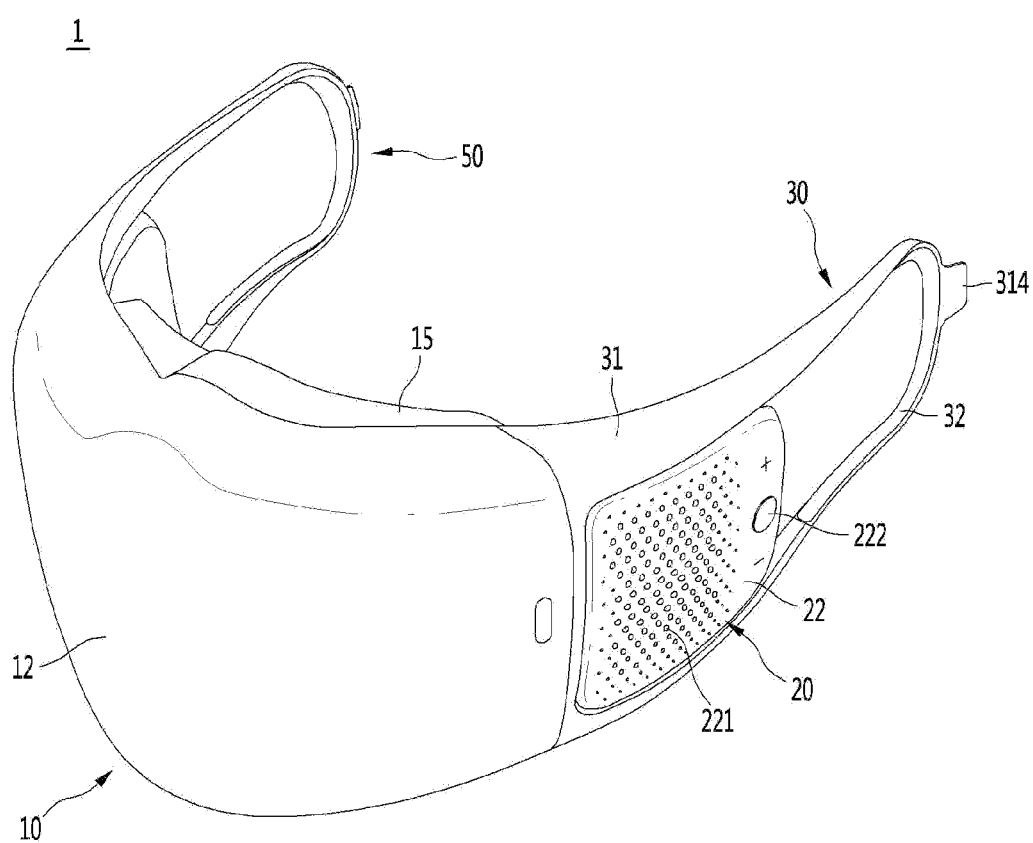

【Figure 2】
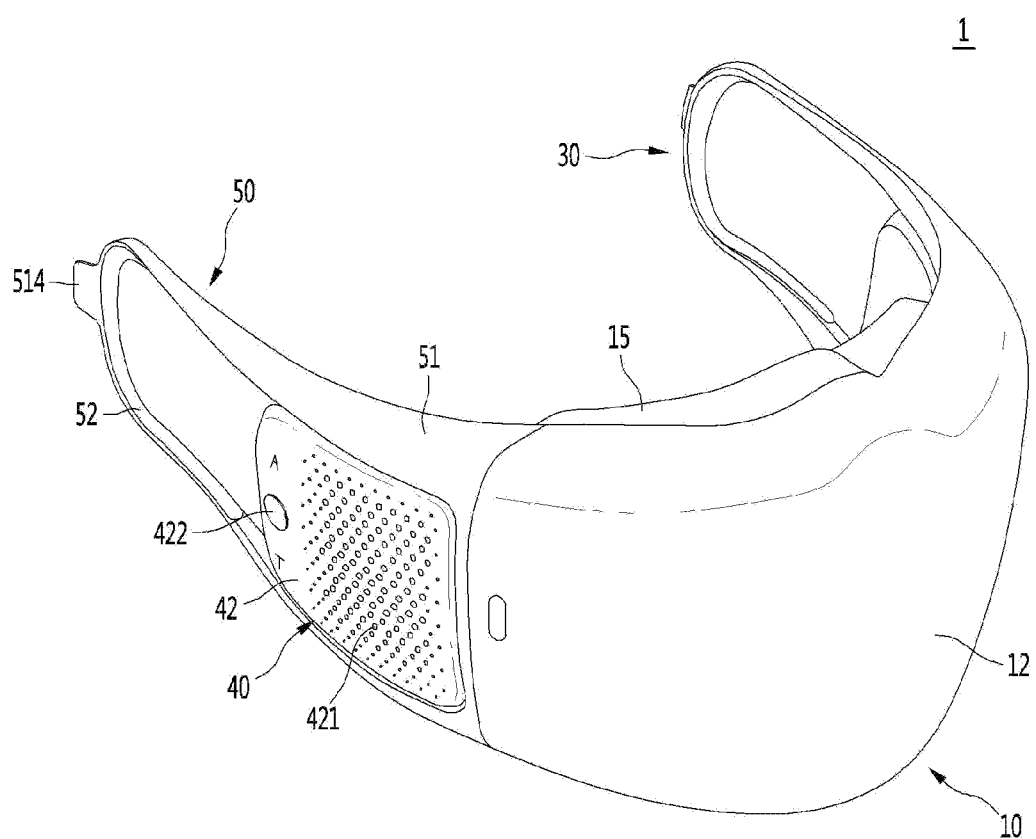

[Figure 3]
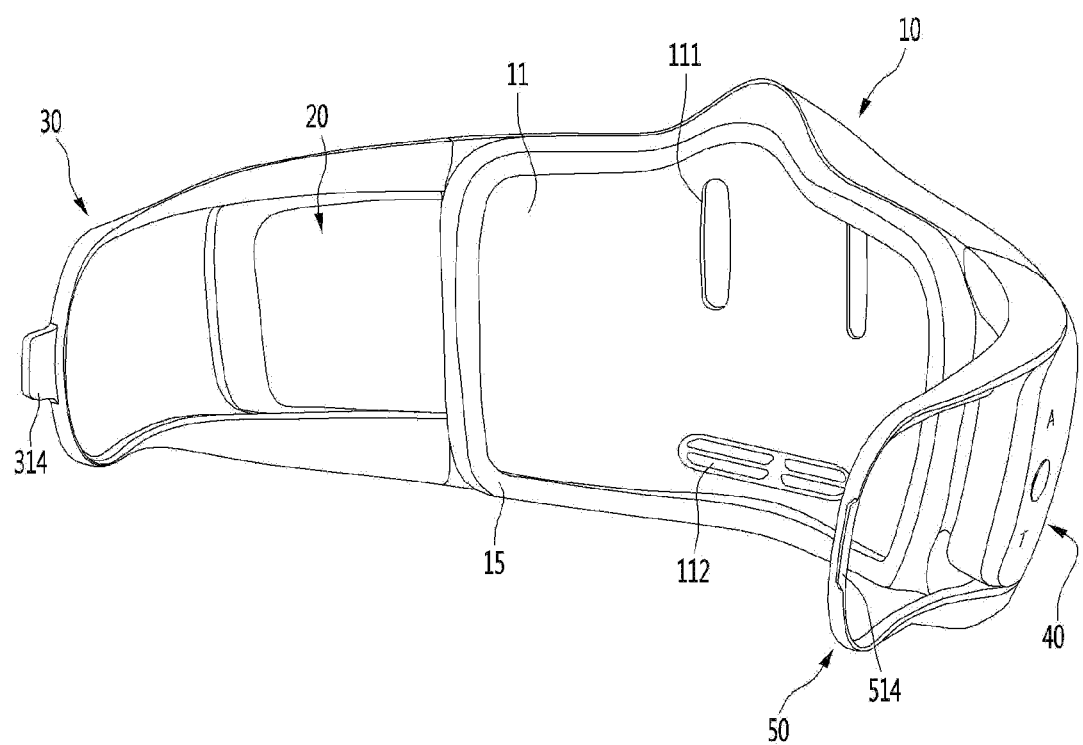

[Figure 4]
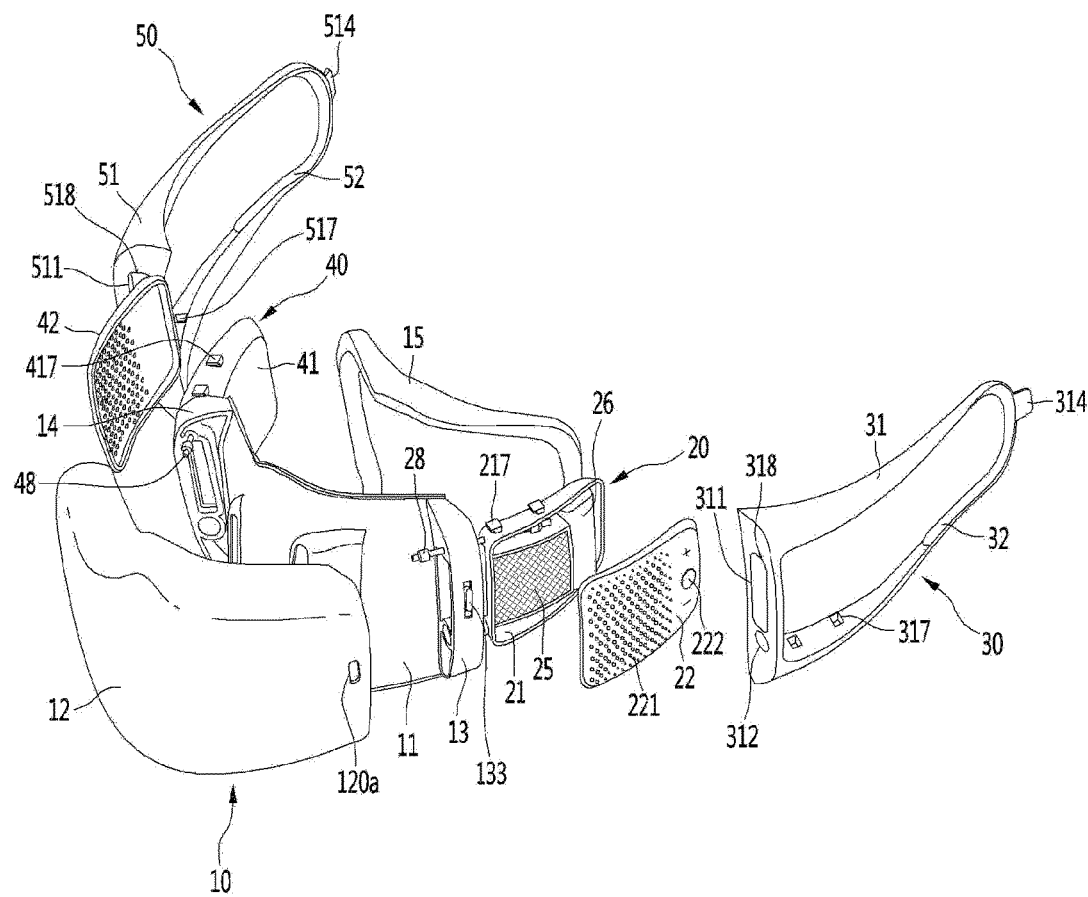

[Figure 5]
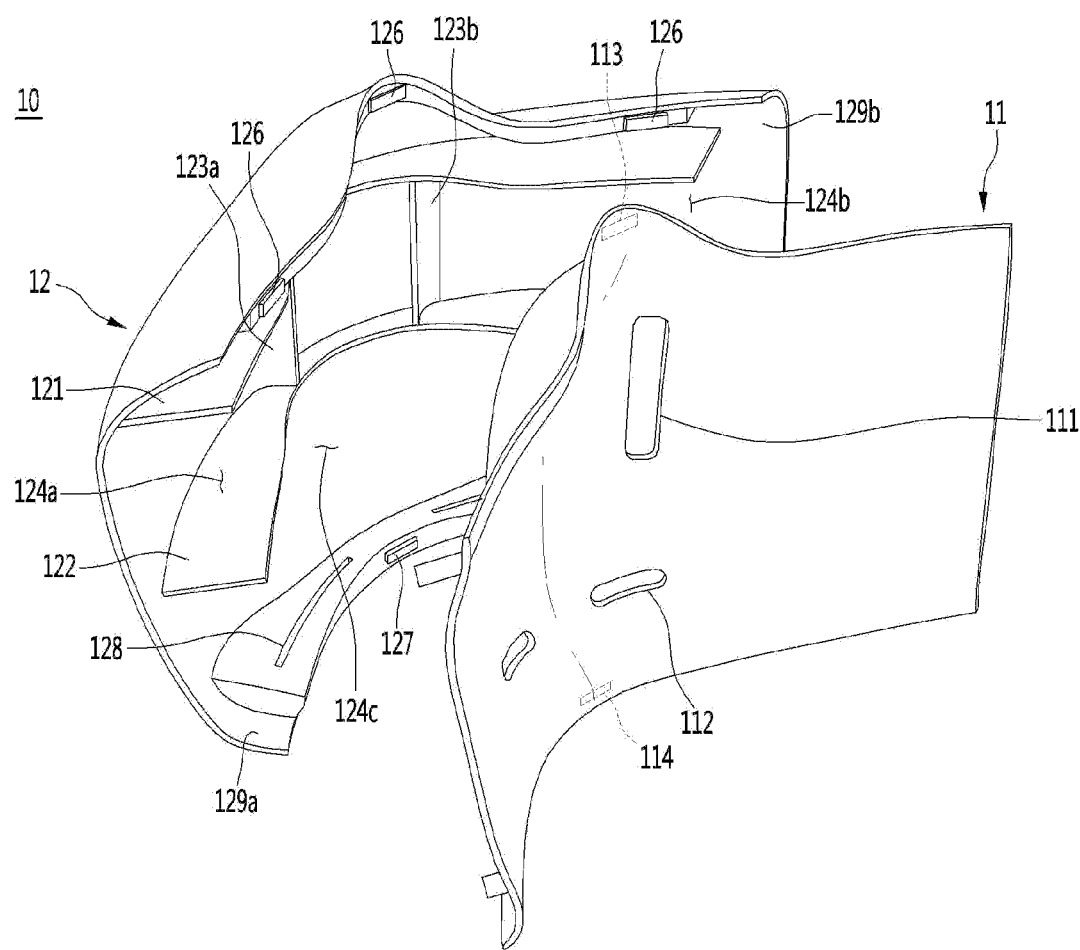

[Figure 6]
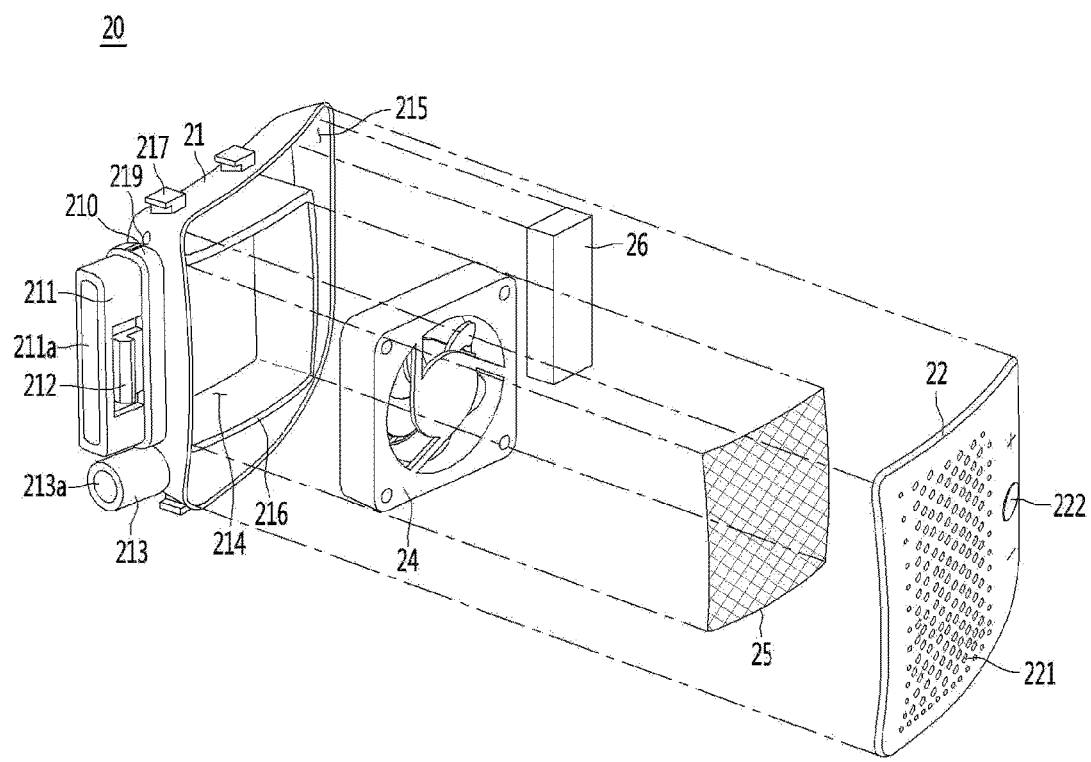

[Figure 7]
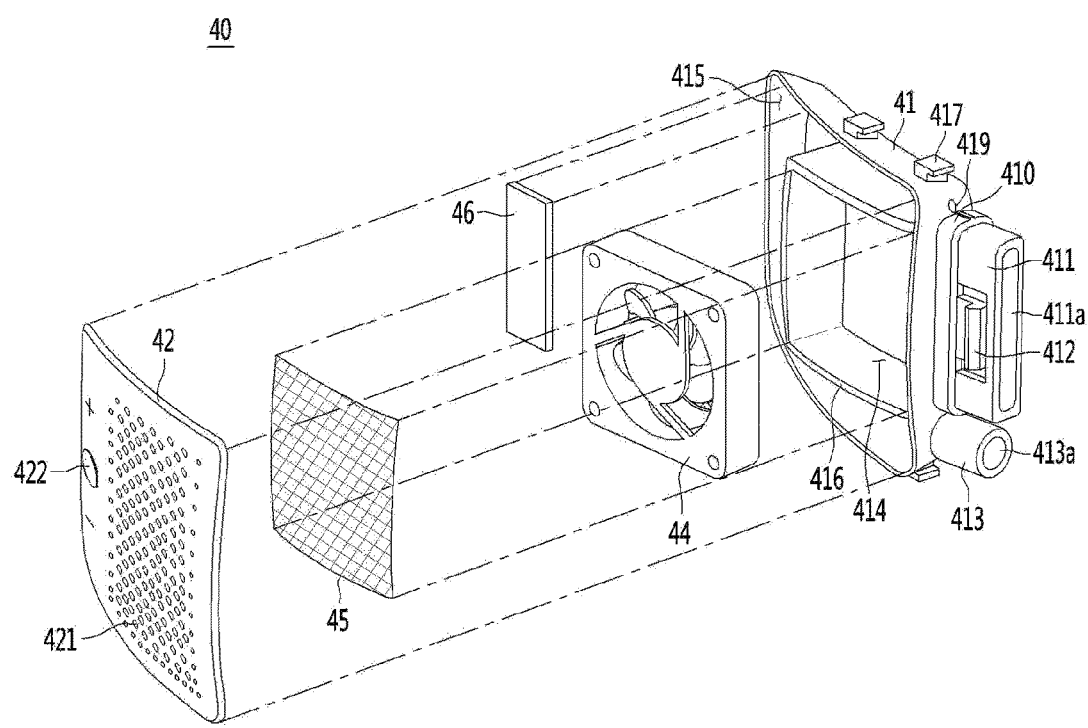

[Figure 8]
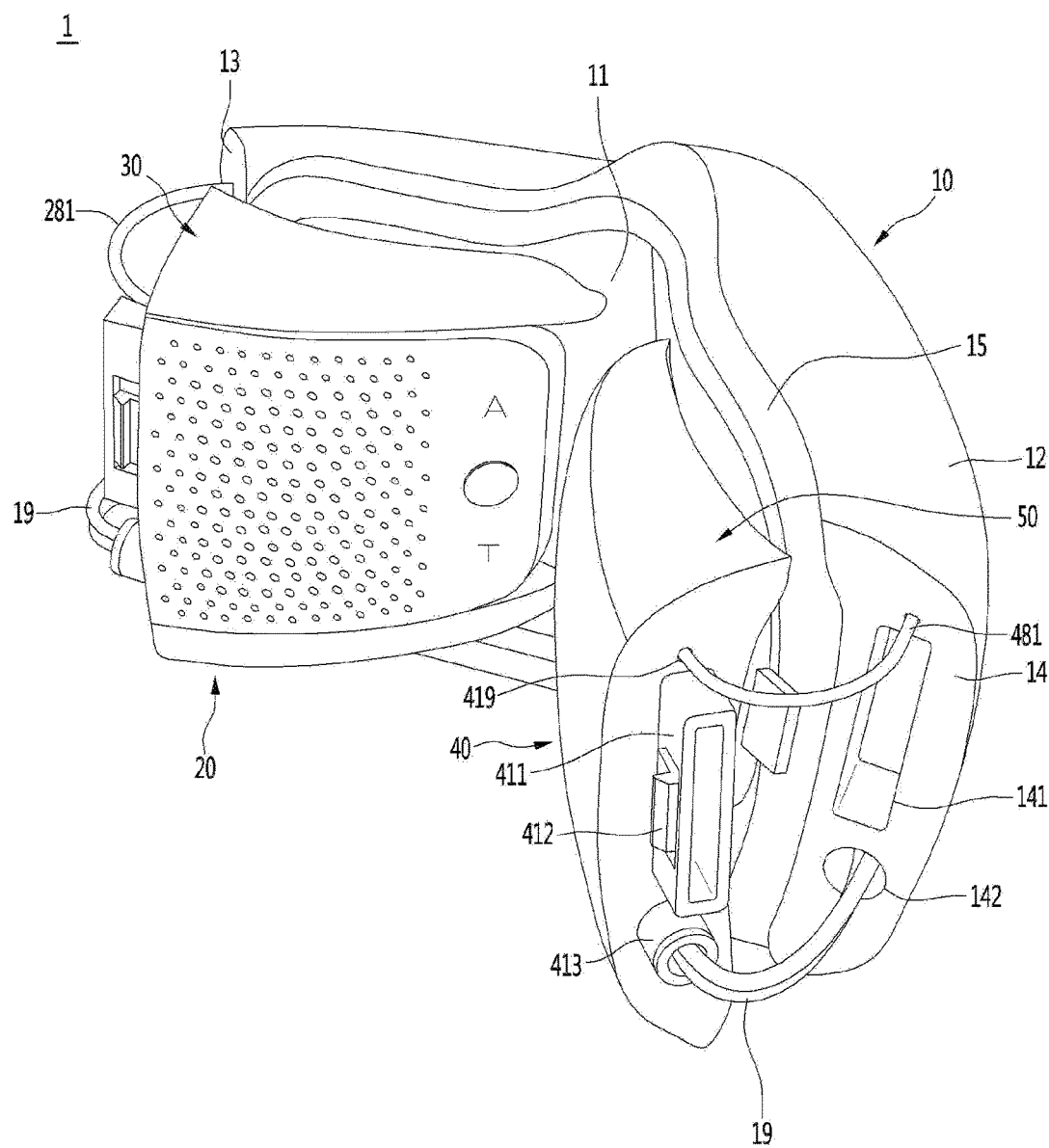

[Figure 9]
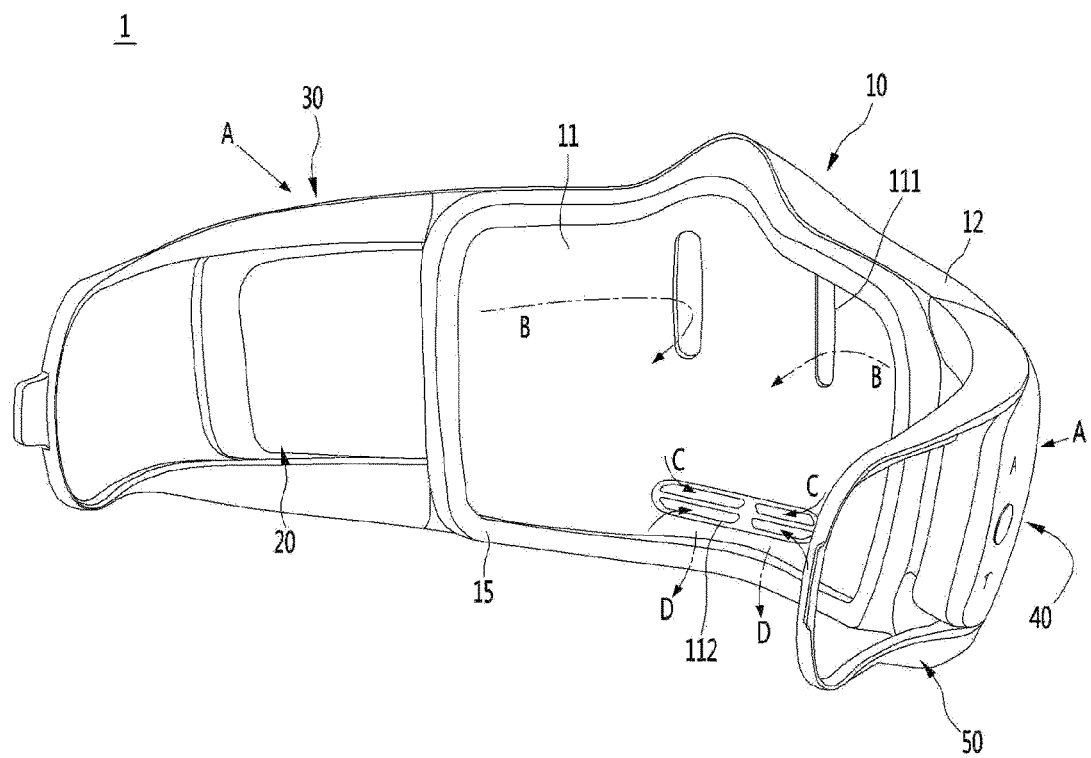

[Figure 10]
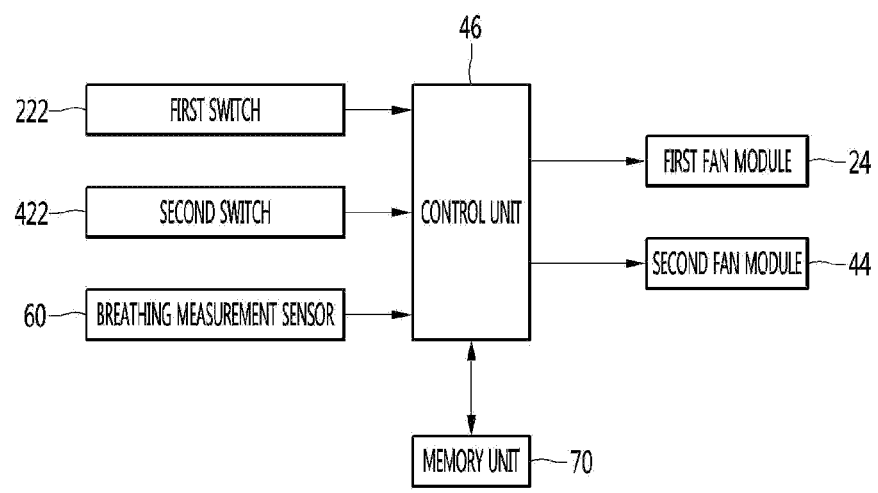

【Figure 11】
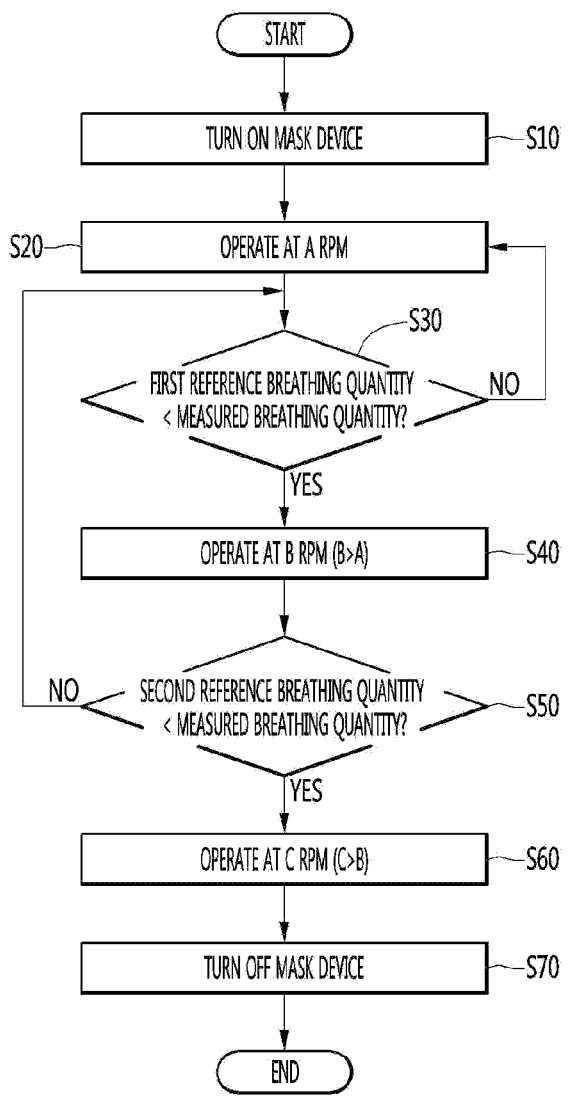

[Figure 12]
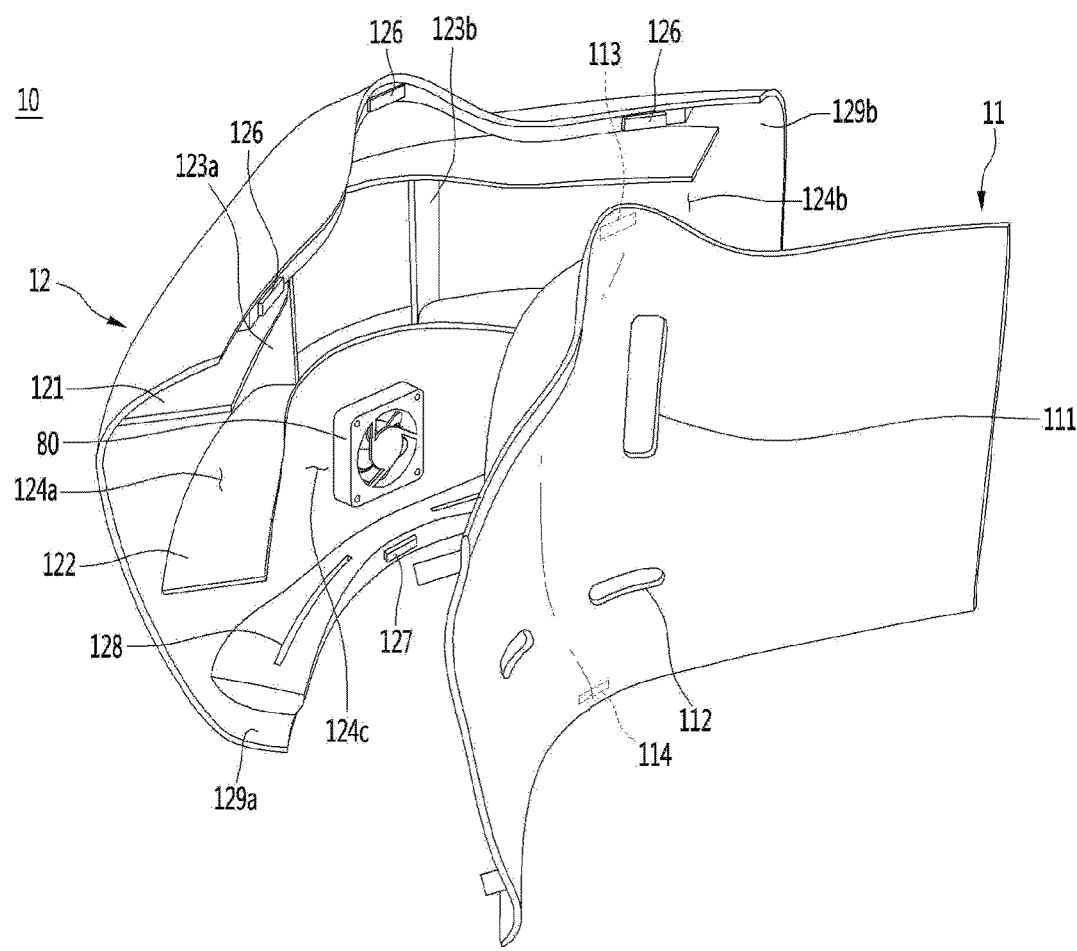

[Figure 13]
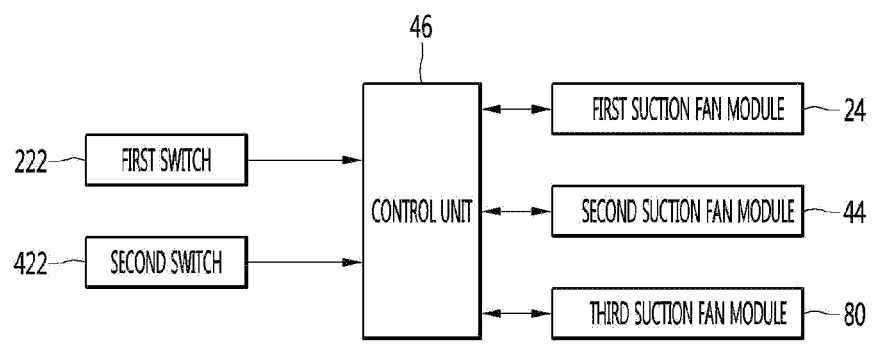

【Figure 14】
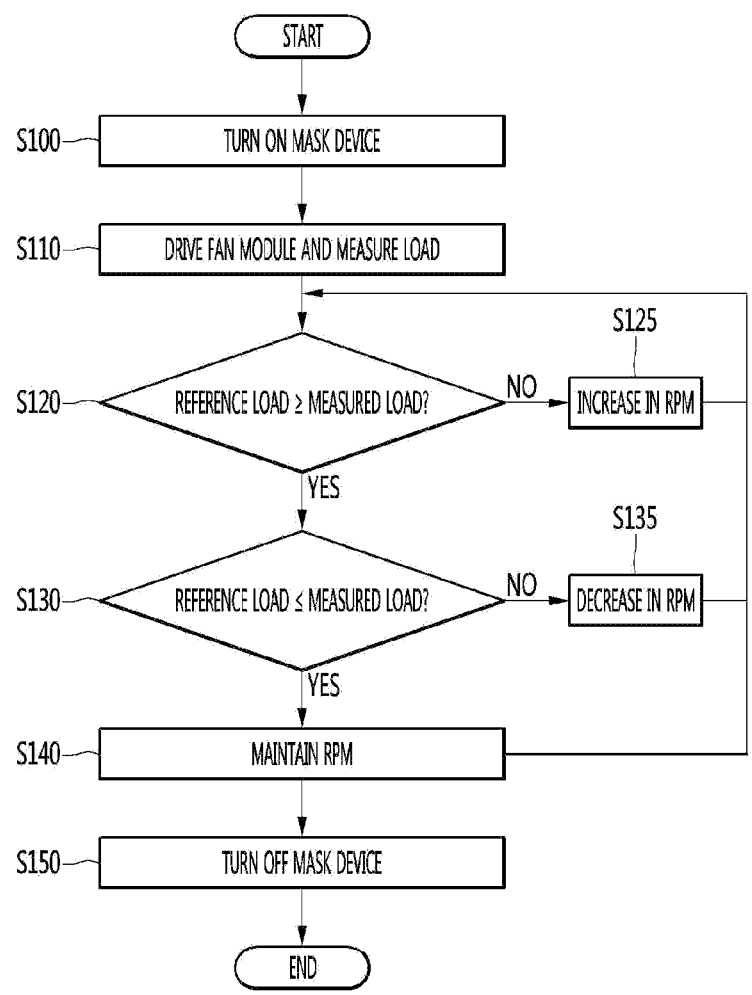

MASK DEVICE AND METHOD FOR CONTROLLING THE SAME

CROSS-REFERENCE TO RELATED APPLICATION

This application is the National Stage filing under 35 U.S.C. 371 of International Application No. PCT/KR2020/000912, filed Jan. 20, 2020, which claims the benefit of Korean Patent Application No. 10-2019-0037323, filed Mar. 29, 2019, the contents of which are all hereby incorporated by reference herein in their entirety.

TECHNICAL FIELD

The present disclosure relates to a mask device and a method for controlling the same.

BACKGROUND ART

In general, a mask device is a device that covers user's nose and mouth to prevent inhalation and scattering of germs and dust. The mask device may be worn to contact the user's face so as to cover the user's nose and mouth.

The mask device filters germs, dust, and the like, which are contained in the air flowing into the user's nose and mouth and is provided so that the filtered air flows into the user's mouth and nose. Here, air, germs, and dust contained in the air are filtered through the mask device provided as a filter.

Here, since air is introduced into the user's nose and mouth through the mask device or is discharged to the outside through the mask device, the user's breathing is not smooth. To solve this limitation, a mask device including a fan forcing a flow of air has recently been developed.

As described above, in regard to the mask device, the following prior art document has been disclosed.

PRIOR ART DOCUMENT 1

1. Patent Registration Number: 20-0422942 (Date of Registration: Aug. 3, 2006)
2. Title of Invention: Dustproof Mask The prior document 1 relates to a dustproof mask that is capable of forcibly suctioning external air into a mask body to allow to feel the comfort of breathing.

In the prior art document 1, the dustproof mask includes a mask body having a suction hole and an exhaust hole defined therein and a suction fan that is coupled to the mask body to forcibly suction external air into the mask body. Also, the dustproof mask includes a filter case for filtering foreign substances contained in the external air forcibly suctioned by rotation of the suction fan.

The prior art document 1 discloses contents of operating or stopping the suction fan. That is, the suction fan is driven at a uniform rotational speed to force a flow of the same amount of air.

The user may wear the mask device to perform various activities. For example, when the user wears the mask device and exercises, the user's breathing quantity may vary greatly. Here, when the mask device forces the flow of the uniform amount of air, there is a limitation that it is very inconvenient for the user.

Also, as the suction fan disclosed in the prior art document 1 is disposed in front of the user, the forced flow of air is introduced directly into the user's nose and mouth. Thus, when the user breathes, it may be difficult to discharge the air, and as a result, the user's breathing is more uncomfortable. Particularly, this limitation is greater as the user's breathing quantity increases.

DISCLOSURE

Technical Problem

Embodiments provide a mask device which controls a rotation speed according a user's breathing quantity to improve user's convenience and a method for controlling the same.

Embodiments also provide a mask device in which an exhaust fan is provided separately from a suction fan to accurately measure a user's breathing quantity, thereby maximizing user's convenience and a method for controlling the same.

Embodiments also provide a mask device in which a sensor for measuring user's breathing is provided to more simply and accurately measure a user's breathing quantity, thereby controlling a suction fan and a method for controlling the same.

Technical Solution

A mask device according to an embodiment measures a user's breathing quantity and changes an RPM of a fan motor according to the measured user's breathing quantity. Here, to measure the user's breathing quantity, there are a method 1) for detecting characteristics of discharged air by using a sensor and a method 2) for detecting a load of an exhaust fan module by providing the exhaust fan module, which is separated from a suction fan motor.

In one embodiment, a mask device includes: a mask body configured to cover a nose and mouth of a user; a first air cleaner connected to one side of the mask body, the first air cleaner being configured to filter air and force a flow of the air; and a second air cleaner connected to the other side of the mask body, the second air cleaner being configured to filter air and force a flow of the air.

The mask device may include a first passage, a second passage, and a third passage, which are partitioned from each other within the mask body.

The mask device may include a first suction fan module installed in the first air cleaner to suction external air so that the external air flows to the first passage; a second suction fan module installed in the second air cleaner to suction external air so that the external air flows to the second passage; and an exhaust fan module disposed in the third passage.

First and second suction fan modules may be installed at a suction-side, and an exhaust fan module may be installed at an exhaust-side.

In another embodiment, a method for controlling a mask device includes: turning the mask device on; and driving a first suction fan module, a second suction fan module, and an exhaust fan module.

Thus, external air may be filtered by driving the first suction fan module and the second suction fan module to flow to the mask body covering the user's nose and mouth so as to be supplied to the user, and the air discharged from the user together with the driving of the exhaust fan module may be discharged to the outside.

Here, the driving of the first suction fan module and the second suction fan module may be understood to force a flow of air so that the external air is suctioned and filtered, and the exhaust fan module may allow the air to flow so that the user breathes smoothly.

The mask device may be turned off, and the driving of the first suction fan module, the second suction fan module, and the exhaust fan module may be stopped.

In the turn-on state of the mask device, the first suction fan module, the second suction fan module, and the exhaust fan module may be changed in rpm according to a load of the exhaust fan module.

When the load of the exhaust fan module increases, it may be determined that the user's breathing quantity increases. Thus, the rpm may increase to allow the air to flow faster so that the user does not feel stuffy.

The details of one or more embodiments are set forth in the accompanying drawings and the description below. Other features will be apparent from the description and drawings, and from the claims.

Advantageous Effects

According to the proposed embodiment, there may be an advantage that the user comfortably breathes regardless of the external situation by changing the amount of air forcibly flowing according to the user's breathing quantity.

Particularly, as the user removes the inconvenience in wearing of the mask device, there may be an advantage that the breathing organ is protected by wearing the mask device in various situations.

Also, since the suction fan and the exhaust fan are separately provided, the user's breathing quantity may be measured more accurately, and the user's convenience may be maximized by forcing the flow of air.

Also, the sensor for measuring the user's breathing may be provided to more simply and accurately measure the breathing quantity, and the user's convenience and simplification of the structure may be realized by forcing the flow of air.

DESCRIPTION OF DRAWINGS

FIGS. 1 to 3 are views of a mask device according to an embodiment.

FIG. 4 is an exploded view of the mask device according to an embodiment.

FIG. 5 is an exploded view illustrating a mask body of the mask device according to an embodiment.

FIG. 6 is an exploded view illustrating a first air cleaner of the mask device according to an embodiment.

FIG. 7 is an exploded view illustrating a second air cleaner of the mask device according to an embodiment.

FIG. 8 is a view illustrating a state in which the mask device is folded according to an embodiment.

FIG. 9 is a view illustrating a flow of air flowing by the mask device according to an embodiment.

FIG. 10 is a view illustrating a configuration for controlling the mask device according to an embodiment.

FIG. 11 is a flowchart illustrating a method for controlling the mask device according to an embodiment.

FIG. 12 is a view of a mask device according to another embodiment.

FIG. 13 is a view illustrating a configuration for controlling the mask device according to another embodiment.

FIG. 14 is a flowchart illustrating a method for controlling the mask device according to another embodiment.

MODE FOR INVENTION

Hereinafter, some embodiments of the present disclosure will be described in detail with reference to the accompanying drawings. It should be noted that when components in the drawings are designated by reference numerals, the same components have the same reference numerals as far as possible even though the components are illustrated in different drawings. In the following description of the present disclosure, a detailed description of known functions and configurations incorporated herein will be omitted to avoid making the subject matter of the present disclosure unclear.

In the description of the elements of the present disclosure, the terms first, second, A, B, (a), and (b) may be used. Each of the terms is merely used to distinguish the corresponding component from other components, and does not delimit an essence, an order or a sequence of the corresponding component. It should be understood that when one component is "connected", "coupled" or "joined" to another component, the former may be directly connected or jointed to the latter or may be "connected", coupled" or "joined" to the latter with a third component interposed therebetween.

FIGS. 1 to 3 are views of a mask device according to an embodiment, and FIG. 4 is an exploded view of the mask device according to an embodiment. In detail, FIG. 1 is a right perspective view of the mask device, FIG. 2 is a left perspective view of the mask device, and FIG. 3 is a rear perspective view of the mask device.

As illustrated in FIGS. 1 to 4, a mask device 1 may include a mask body 10. The mask body 10 may contact a user's face. The mask body 10 may contact the user's face to cover user's mouth and nose.

The mask body 10 may include a frame 11 and a front cover 12. The frame 11 and the front cover 12 may be detachably coupled to each other. The frame 11 may define a portion of the mask body 10. The front cover 12 may define a portion of the remaining part of the mask body 10.

Here, a portion of the mask body 10 may be disposed in a direction toward the user's nose and mouth. The remaining portion of the mask body 10 may be disposed in a direction toward an external space. The frame 11 may be disposed in front of the user's nose and mouth and may define a space through which air flowing into the user's nose and mouth passes. The front cover 12 may be disposed in a direction toward the external space and may define an outer appearance of the mask body 10.

The frame 11 may include an inflow hole 111 and an outflow hole 112. The inflow hole 111 may be understood as an opening for supplying air filtered by a first air cleaner 20 and a second air cleaner 40 to be described later in a direction toward the user's nose and mouth. The outflow hole 112 may be understood as an opening for discharging air discharged from the user's nose and mouth to the external space.

In this embodiment, the inflow hole 111 may be defined in front of the user's nose. The outflow hole 112 may be defined in front of the user's mouth. An arranged position of each of the inflow hole 111 and the outflow hole 112 may be various changed according to situations.

In this embodiment, the inflow hole 111 may be defined with an opening larger than the outflow hole 112 to facilitate an inflow of filtered air. The sizes of the inflow hole 111 and the outflow hole 112 may be variously changed according to the situations. The air flowing through the inflow hole 111 and the air flowing through the outflow hole 112 may flow in a state of being separated from each other in the mask body 10.

The mask body 10 may include a first fixing part 13 and a second fixing part 14. The first fixing part 13 and the second fixing part 14 may allow the first air cleaner 20 and the second air cleaner 40, which will be described below, to be fixed to the mask body 10.

In this embodiment, the first fixing part 13 may be disposed at a left side of the mask body 10, and the second fixing part 14 may be disposed at a right side of the mask body 10. The position of each of the first fixing part 13 and the second fixing part 14 may be variously changed according to the situations.

The first fixing part 13 and the second fixing part 14 may be disposed between the front cover 12 and the frame 11. A portion of each of the first fixing part 13 and the second fixing part 14 may be fixed to the front cover 12. For example, a hook 133 of the first fixing part 13 and a hook groove 120a of the front cover 12 may be detachably coupled to each other. The remaining portion of each of the first fixing part 13 and the second fixing part 14 may be fixed to the frame 11.

The first fixing part 13 may be inserted and fixed in an inner direction of the mask body 10 at a left end of the mask body 10. The second fixing part 14 may be inserted and fixed in the inner direction of the mask body 10 at a right end of the mask body 10.

The mask body 10 may include a packing 15. The packing 15 may be fixed to the frame 11. The packing 15 may be inserted or interposed between the frame 11 and the user's face when the mask body 10 contacts the user's face. The packing 15 may be made of a material that is deformed into a shape corresponding to the user's face when contacting the user's face.

Also, the packing 15 may be detachably mounted to the frame 11. For example, the packing 15 may be partially inserted into the frame 11 or may be attached and fixed to one side of the frame 11. That is, the packing 15 may be deformed to correspond to the user's face to minimize an occurrence of the gap between the frame 11 and the user's face.

The mask device 1 may include a first air cleaner 20 and a second air cleaner 40. The first air cleaner 20 and the second air cleaner 40 may be disposed on both sides of the mask body 10, respectively. In this embodiment, the first air cleaner 20 may be disposed on a left side of the mask body 10, and the second air cleaner 40 may be disposed on a right side of the mask body 10.

The first air cleaner 20 and the second air cleaner 40 may be fixed to the first fixing part 13 and the second fixing part 14 of the mask body 10, respectively. The first air cleaner 20 and the second air cleaner 40 may move with respect to the first fixing part 13 and the second fixing part 14, respectively.

For example, the first air cleaner 20 may be folded with respect to the first fixing part 13, and the second air cleaner 40 may be folded with respect to the second fixing part 14. Although the first air cleaner 20 and the second air cleaner 40 are described as being folded with respect to the first fixing part 13 and the second fixing part 14 in this embodiment, it may be understood that the first air cleaner 20 and the second air cleaner 40 are rotatable.

When the first air cleaner 20 and the second air cleaner 40 are folded toward the mask body 10, a volume of each of the first air cleaner 20 and the second air cleaner 40 may be minimized to facilitate the storage of the mask device 1. Also, when the first air cleaner 20 and the second air cleaner 40 are folded away from the mask body 10, the first air cleaner 20 and the second air cleaner 40 are optimized to the shape of the user's face. Thus, foreign substances in the external space may be minimally introduced into the space in which the user's nose and mouth are disposed.

The first air cleaner 20 and the second air cleaner 40 may suction air in the external space to filter the suctioned air. The filtered air may be introduced into the mask body 10 and be supplied to the user's nose and mouth through the inflow hole 111. The air filtered by each of the first air cleaner 20 and the second air cleaner 40 is supplied to the inflow hole 111.

The first air cleaner 20 may include a first cleaner body 21 and a first cleaner cover 22. The first cleaner body 21 and the first cleaner cover 22 may be detachably coupled to each other. When the first cleaner cover 22 is separated from the first cleaner body 21, components stored in the first cleaner body 21 may be exposed to the outside.

The first cleaner body 21 may have a space in which a plurality of components are accommodated. A first fan module 24 (see FIG. 6) and a first filter module 25 may be disposed in the first cleaner body 21. The first fan module 24 may generate a suction force for suctioning the external air. The first filter module 25 may filter the foreign substances from the suctioned air.

The first filter module 25 may be disposed upstream of the first fan module 24 based on a flow direction of air. The first filter module 25 may be disposed downstream of the first fan module 24 based on the flow direction of air, but is preferably disposed upstream of the first fan module 24.

A battery 26 may be disposed in the first cleaner body 21. The battery 26 may supply power for operating the first air cleaner 20. Also, the battery 26 may supply power for operating a second air cleaner 40 that will be described later.

In this embodiment, the first air cleaner 20 and the second air cleaner 40 may receive power by one battery 26. When the battery 26 is disposed inside one of the first air cleaner 20 and the second air cleaner 40, a circuit board 46 (see FIG. 7) for operating the first air cleaner 20 and the second air cleaner 40 may be disposed in the remaining air cleaner. That is, the battery 26 and the circuit board 46 corresponding to a load of the battery 26 may be disposed inside the different air cleaners so that the mask device 1 is balanced.

The mask device 1 may include a first departure prevention part 28. The first departure prevention part 28 may connect the first fixing part 13 to the first cleaner body 21. The first departure prevention part 28 may have a predetermined length. The first departure prevention part 28 may prevent the first cleaner body 21 from being separated from the first fixing part 13.

The first departure prevention part 28 may be provided in plurality in the mask device 1. For example, the first departure prevention part 28 may be disposed to be spaced apart from the first fixing part 13 and the first cleaner body 21 in the vertical direction between the first fixing part 13 and the first cleaner body 21. One end of the first departure prevention part 28 may be fixed to the first fixing part 13. The other end of the first departure prevention part 28 may be fixed to the first cleaner body 21. That is, the first cleaner body 21 may move with respect to the first fixing part 13 by the first departure prevention part 28.

The first departure prevention part 28 may be separated from the first fixing part 13 or the first cleaner body 21. When the first departure prevention part 28 is separated from the first fixing part 13 or the first cleaner body 21, the first air cleaner 20 may be separated from the mask body 10. Also, when the first air cleaner 20 is separated from the mask body 10, the first ear hook part 30, which will be described later, may be mounted on the first air cleaner 20.

The first cleaner cover 22 includes a first suction hole 221 and a first switch 222. The first suction hole 221 may be understood as an opening through which air in the external space is suctioned. The Air passing through the first suction hole 221 may pass through the inflow hole 111. The first suction hole 221 may be provided in a plurality of openings. The first switch 222 may be understood as a manipulation switch for operating the first air cleaner 20. Also, the first switch 222 may operate as a manipulation switch for operating the second air cleaner 40.

The second air cleaner 40 may include a second cleaner body 41 and a second cleaner cover 42. The second cleaner body 41 and the second cleaner cover 42 may be detachably coupled to each other. When the second cleaner cover 42 is separated from the second cleaner body 41, components stored in the second cleaner body 41 may be exposed to the outside.

The second cleaner body 41 may have a space in which a plurality of components are accommodated. A second fan module 44 (see FIG. 7) and a second filter module 45 (see FIG. 7) may be disposed in the second cleaner body 41. The second fan module 44 may generate a suction force for suctioning the external air. The second filter module 45 may filter the foreign substances from the suctioned air.

The second filter module 45 may be disposed upstream of the second fan module 44 based on a flow direction of air. The second filter module 45 may be disposed downstream of the second fan module 44 based on the flow direction of air, but is preferably disposed upstream of the second fan module 44.

The circuit board 46 (see FIG. 7) may be disposed in the second cleaner body 41. The circuit board 46 may control an operation of one or more of the first air cleaner 20 and the second air cleaner 40. In this embodiment, the first air cleaner 20 and the second air cleaner 40 may be controlled by the circuit board 46.

The mask device 1 may include a second departure prevention part 48. The second departure preventing unit 48 may connect the second fixing part 14 to the second cleaner body 41. The second departure prevention part 48 may have a predetermined length. The second departure prevention part 48 may prevent the second cleaner body 41 from being separated from the second fixing part 14.

The second departure preventing unit 48 may be provided in plurality in the mask device 1. For example, the second departure prevention part 48 may be disposed to be spaced apart from the second fixing part 14 and the second cleaner body 41 in the vertical direction between the second fixing part 14 and the second cleaner body 41. One end of the second departure prevention part 48 may be fixed to the second fixing part 14. The other end of the second departure prevention part 48 may be fixed to the second cleaner body 41. That is, the second cleaner body 41 may move with respect to the second fixing part 14 by the second departure preventing part 48.

The second departure prevention part 48 may be separated from the second fixing part 14 or the second cleaner body 41. When the second departure prevention part 48 is separated from the second fixing part 14 or the second cleaner body 41, the second air cleaner 40 may be separated from the mask body 10. Also, when the second air cleaner 40 is separated from the mask body 10, the second ear hook part 50, which will be described later, may be mounted on the second air cleaner 40.

The second cleaner cover 42 may include a second suction hole 421 and a second switch 422. The second suction hole 421 may be understood as an opening through which air in an external space is suctioned. The Air passing through the first suction hole 421 may pass through the inflow hole 111. The second suction hole 421 may be provided in a plurality of openings. The second switch 422 may be understood as a manipulation switch for operating the second air cleaner 40. Also, the second switch 422 may be understood as a manipulation switch for operating the second air cleaner 20.

The mask device 2 may include a first ear hook part 30 and a second ear hook part 50. The first ear hook part 30 and the second ear hook part 50 may be detachably mounted on the first air cleaner 20 and the second air cleaner 40, respectively. The first ear hook part 30 may be mounted on the first air cleaner 20, and the second ear hook part 50 may be mounted on the second air cleaner 40.

The first ear hook part 30 may be fixed to the left ear of the user, and the second ear hook part 50 may be fixed to the right ear of the user. The first air cleaner 20 and the second air cleaner 40 are fixed to the mask body 10 so that the mask body 10 is fixed to the user's face by the first ear hook part 30 and the second ear hook part 50.

The first ear hook part 30 includes a first hook body 31 forming a body. The first hook body 31 may be fixed to the user's ear. For example, the first hook body 31 may be provided in a strap shape and be fixed to the user's ear.

Here, one side of the first hook body 31 may be fixed to the first air cleaner 20, and the other side of the first hook body 31 may be fixed to the user's ear. The first hook body 31 tensions or contracts a length of the first hook body 31 between the first air cleaner 20 and the user's ear so that the mask body 10 contacts the user's face.

The first hook body 31 may include a first duct through-hole 311 and a first wire tube through-hole 312 into which a portion of the first air cleaner 20 is inserted. The first duct through-hole 311 may be understood as an opening into which the first duct 211 (see FIG. 6) of the first cleaner body 21, which will be described later, is inserted. The first wire tube through-hole 312 may be understood as an opening into which the first wire tube 213 (see FIG. 6) of the first cleaner body 21, which will be described later, is inserted. When the first duct 211 and the first wire tube 213 are inserted into the first duct through-hole 311 and the first wire tube through-hole 312, the first air cleaner 20 may be fixed to one side of the first hook body 31.

The first hook body 31 may include a first hook catching groove 317 in which a portion of the first air cleaner 20 is fixed. The first hook catching groove 317 may be provided in plurality. The first hook catching groove 317 may be understood as an opening through which a first hook 217 of the first cleaner body 21 is looked to be fixed. When the first hook 217 is coupled to the first hook catching groove 317, the first cleaner body 21 may be fixed to the first hook body 31. When the first hook 217 is separated from the first hook catching groove 317, the first cleaner body 21 may be separated from the first hook body 31.

The first hook body 31 may include a first handle 314. The first handle 314 may be understood as a portion held by the user's hand when the first hook body 31 is mounted on the user's ear. The first handle 314 may be provided on the other side of the first hook body 31 hooked to be fixed to the user's ear. A portion of the first hook body 31 protrudes to provide the first handle 314.

The first hook body 31 may include a first contact part 32. The first contact part 32 may be understood as a portion that contacts the user's ear when the first hook body 31 is mounted on the user's ear. The first contact part 32 may contact the user's ear to minimize a pressure applied by the first hook body 31 to the user's ear. The first contact part 32 may be disposed to be inserted between a user's ear and an inner surface of the first hook body 31. The first contact part 32 may be provided on the inner surface of the first hook body 31 contacting the user's ear.

The first hook body 31 may include a first strap through-hole 318. The first string through-hole 318 may be understood as an opening through which a first departure prevention string 281 (see FIG. 8) of the first departure prevention part 28 passes. The first strap through-hole 318 may be defined in a size and shape corresponding to the first departure prevention strap 281.

The first departure prevention strap 281 may connect the mask body 10 to the first air cleaner 20. In detail, the first departure prevention strap 281 may connect the first fixing part 13 of the mask body 10 to the first cleaner body 21 of the first air cleaner 20. Here, a portion of the first departure prevention strap 281 connecting the first fixing part 13 to the first cleaner body 21 may pass through the first strap through-hole 318.

The second ear hook part 50 may include a second hook body 51 forming a body. The second hook body 51 may be fixed to the user's ear. For example, the second hook body 51 may be provided in a strap shape and be fixed to the user's ear.

Here, one side of the second hook body 51 may be fixed to the second air cleaner 40, and the other side of the second hook body 51 may be fixed to the user's ear. The second hook body 51 tensions or contracts a length of the second hook body 51 between the second air cleaner 40 and the user's ear so that the mask body 10 contacts the user's face.

The second hook body 51 may include a second duct through-hole 511 and a second wire tube through-hole (not shown) into which a portion of the second air cleaner 40 is inserted. The second duct through-hole 511 may be understood as an opening into which the second duct 411 (see FIG. 7) of the second cleaner body 41, which will be described later, is inserted. The second wire tube through-hole may be understood as an opening into which the second wire tube 413 (see FIG. 7) of the second cleaner body 41, which will be described below, is inserted. When the second duct 411 and the second wire tube 413 are inserted into the second duct through-hole 511 and the second wire tube through-hole, the second air cleaner 40 may be fixed to one side of the second hook body 51.

The second hook body 51 may include a second hook catching groove 517 in which a portion of the second air cleaner 40 is fixed. The second hook catching grooves 517 may be provided in plurality. The second hook catching groove 517 may be understood as an opening through which the second hook 417 of the second cleaner body 41 is hooked.

When the second hook 417 is coupled to the second hook catching groove 517, the second cleaner body 41 may be fixed to the second hook body 51. When the second hook 417 is separated from the second hook catching groove 517, the second cleaner body 41 may be separated from the second hook body 51.

The second hook body 51 may include a second handle 514. The second handle 514 may be understood as a portion held by the user's hand when the second hook body 51 is mounted on the user's ear. The second handle 514 may be provided on the other side of the second hook body 51 that is fixed to the user's ear. A portion of the second hook body 51 protrudes to provide the second handle 514.

The second hook body 51 may include a second contact part 52. The second contact part 52 may be understood as a portion contacting the user's ear when the second hook body 51 is mounted on the user's ear. The second contact part 52 may contact the user's ear to minimize a pressure applied by the second hook body 51 to the user's ear. The second contact part 52 may be disposed to be inserted between the user's ear and the inner surface of the second hook body 51. The second contact part 52 may be provided on the inner surface of the second hook body 51 contacting the user's ear.

The second hook body 51 may include a second strap through-hole 518. The second strap through-hole 518 may be understood as an opening through which the second departure prevention strap 481 (FIG. 8) of the second departure prevention part 48 to be described later passes. The second strap through-hole 518 may be defined in a size and shape corresponding to the second departure prevention strap 481.

The second departure prevention strap 481 may connect the mask body 10 to the second air cleaner 40. The second departure prevention strap 481 may connect the second fixing part 14 of the mask body 10 to the second cleaner body 41 of the second air cleaner 40. Here, a portion of the second departure prevention strap 481 connecting the second fixing part 14 to the second cleaner body 41 may pass through the second strap through-hole 518.

Hereinafter, respective configurations of the mask device 1 is demonstrated in detail with reference to the accompanying drawings.

FIG. 5 is an exploded view illustrating the mask body of the mask device according to an embodiment.

As illustrated in FIG. 5, the frame 11 and the front cover 12 may be detachably coupled to each other. In this embodiment, the front cover 12 will be described as being separated from or coupled to the frame 11.

A passage through which air passes may be provided between the frame 11 and the front cover 12. The passage may include a passage through which air passing through the inflow hole 111 of the frame 11 flows and a passage through which air passes through the outflow hole 112 of the frame 11 flows.

A partition plate for providing a passage between the frame 11 and the front cover 12 may be provided. The partition plate may be provided on at least one of the frame 11 or the front cover 12. The partition plate may define a passage by partitioning a space between the front cover 12 and the frame 11 when the front cover 12 is coupled to the frame 11. In this embodiment, the partition plate is described as being provided on the front cover 12.

The partition plate may include a first partition plate 121 and a second partition plate 122. The first partition plate 121 and the second partition plate 122 may protrude from the front cover 12. The first partition plate 121 and the second partition plate 122 may protrude in a direction toward the frame 11 from one surface of the front cover 12 facing the frame 11. The first partition plate 121 and the second partition plate 122 may protrude in a direction toward the frame 11 to contact the frame 11. Each of the first partition plate 121 and the second partition plate 122 may have an adjustable protruding length to correspond to the frame 11.

In this embodiment, the second partition plate 122 may partition a space between the front cover 12 and the frame 11 into an upper space and a lower space. Also, the first partition plate 121 may be disposed above the second partition plate 122.

A first passage 124a and a second passage 124b may be provided between the first partition plate 121 and the second partition plate 122. The first partition plate 121 may partition the upper space into a space in which the first passage 124a and the second passage 124b are provided and a space in which the passage is not provided.

The first passage 124*a* and the second passage 124*b* may be understood as passages through which air flowing to the inflow hole 111 passes. A third passage 124*c* may be provided in the lower space. The third passage 124*c* may be understood as a passage through which air is discharged to the outflow hole 112 and flows toward the discharge hole 128 to be described later.

In this embodiment, the second partition plate 122 may partition the first passage 124*a*, the second passage 124*b*, and the third passage 124*c*. The first partition plate 121 may partition the upper space into the first passage 124*a*, the second passage 124*b*, and a space in which the passage is not provided.

Here, the space in which the passage is not provided may be understood as a space in which a wire 19 (see FIG. 8) connecting the first air cleaner 20 to the second air cleaner 40 is disposed. Alternatively, the space in which the passage is not provided may be understood as a space for securing a space in which the user's nose is seated. The first partition plate 121 and the second partition plate 122 may function as ribs for reinforcing strength of the front cover 12.

A first inflow guide 123*a* and a second inflow guide 123*b* may be provided between the first partition plate 121 and the second partition plate 122. The first inflow guide 123*a* and the second inflow guide 123*b* may protrude between the first partition plate 121 and the second partition plate 122.

The first inflow guide 123*a* and the second inflow guide 123*b* may connect the first partition plate 121 to the second partition plate 122. The first inflow guide 123*a* and the second inflow guide 123*b* partition the space between the first partition plate 121 and the second partition plate 122 into the first passage 124*a* and the second passage. 124*b*.

In this embodiment, the first passage 124*a* may be disposed in the left direction of the mask body 10, and the second passage 124*b* may be disposed in the right direction of the mask body 10. The first inflow guide 123*a* may guide the air passing through the first air cleaner 20 to the left inflow hole of the plurality of inflow holes 111. The second inflow guide 123*b* may guide the air passing through the second air cleaner 40 to the right inflow hole of the plurality of inflow holes 111.

The first inflow guide 123*a* and the second inflow guide 123*b* may be inclined in a direction toward the plurality of inflow holes 111. Also, the first inflow guide 123*a* and the second inflow guide 123*b* contact the frame 11 to partition the space into the first passage 124*a* and the second passage 124*b* when the front cover 12 and the frame 11 are coupled to the first passage 124*a*.

The air passing through the plurality of outflow holes 112 may be introduced into the third passage 124*c*. Also, the discharge hole 128 may be provided to discharge the air introduced into the third passage 124*c* to the external space. The discharge hole 128 may be defined in one of the front cover 12 and the frame 11. In this embodiment, the discharge hole 128 will be described as being defined in the front cover 12.

The discharge hole 128 may be understood as an opening through which the air passing through the third passage 124*c* is discharged to the external space. In this embodiment, the discharge hole 128 may be defined in a lower portion of the front cover 12. When the discharge hole 128 is defined in the lower portion of the front cover 12, it is possible to minimize mixing of the air discharged from the mask device 1 with the air suctioned into the mask device 1. The arranged position of the discharge hole 128 may be variously changed.

A check valve may be provided in one of the discharge hole 128 and the outflow hole 112. The check valve may prevent the external air from flowing back into the mask device 1. In detail, the check valve may prevent unfiltered external air from being introduced into the user's nose and mouth through one of the discharge hole 128 and the outflow hole 112.

The check valve may be closed when the user suctions the filtered air to prevent the external air from flowing to one of the discharge hole 128 and the outflow hole 112. The check valve may be opened to discharge the air suctioned by the user to the external space.

The front cover 12 may include an upper coupling hole 126 and a lower coupling hole 127. Each of the upper coupling hole 126 and the lower coupling hole 127 may be provided in plurality. The upper coupling hole 126 may be defined in an upper portion of the front cover 12. The plurality of upper coupling holes 126 may be spaced apart from each other. The lower coupling hole 127 may be disposed in a lower portion of the front cover 12. The plurality of lower coupling holes 127 may be spaced apart from each other.

The frame 11 may include an upper fixing hole 113 and a lower fixing hole 114. Each of the lower fixing hole 114 and the lower fixing hole 114 may be provided in plurality. The upper fixing hole 113 may be disposed in an upper portion of the frame 11. The plurality of upper fixing holes 113 may be spaced apart from each other. The lower fixing hole 114 may be disposed in a lower portion of the frame 11

The plurality of lower fixing holes 114 may be spaced apart from each other. The upper fixing hole 113 may be defined in a position corresponding to the upper coupling hole 126, and the lower fixing hole 114 may be defined in a position corresponding to the upper coupling hole 126.

In this embodiment, the upper fixing hole 113, the lower fixing hole 114, the upper coupling hole 126, and the lower coupling hole 127 may be provided as magnet members. Alternatively, each of the upper coupling hole 126 and the lower coupling hole 127 may be provided as a coupling member, and each of the upper fixing hole 113 and the lower fixing hole 114 may be provided as a coupling groove to which the coupling member is coupled.

The front cover 12 and the frame 11 may include a first fixing part seating groove 129*a* and a second fixing part seating groove 129*b*. The first fixing part 13 may be fixed to the first fixing part seating groove 129*a*. The second fixing part 14 may be fixed to the second fixing part seating groove 129*b*.

The first fixing part seating groove 129*a* and the second fixing part seating groove 129*b* may be defined between the front cover 12 and the frame 11. In this embodiment, the first fixing part seating groove 129*a* may be provided in a left end of the mask body 10. The second fixing part seating groove 129*b* may be provided in a right end of the mask body 10. The first fixing part seating groove 129*a* may be provided with a fixing unit for fixing the first fixing part 13. The second fixing part seating groove 129*b* may be provided with a fixing unit for fixing the second fixing part 14.

The mask body 10 may further include a fragrance module for supplying fragrance. The fragrance module may be provided on one of the front cover 12 and the frame 11. For example, the fragrance module may provide the fragrance to air introduced into the user's nose and mouth through the first passage 124*a* and the second passage 124*b*. Here, the fragrance module may be provided in the first passage 124*a* and the second passage 124*b*. The fragrance module may be configured to be replaced when the front cover 12 and the frame 11 are separated.

FIG. 6 is an exploded view illustrating the first air cleaner of the mask device according to an embodiment, and FIG. 7 is an exploded view illustrating the second air cleaner of the mask device according to an embodiment.

The first air cleaner 20 and the second air cleaner 40 illustrated in FIGS. 6 and 7 may suction the external air from both sides of the mask body 10. The air suctioned into the first air cleaner 20 and the second air cleaner 40 may be filtered inside the first air cleaner 20 and the second air cleaner 40.

The filtered air may be supplied to the user's nose and mouth after passing through the first passage 124a and the second passage 124b of the mask body 10. The first air cleaner 20 and the second air cleaner 40 may operate in the same manner. The first air cleaner 20 and the second air cleaner 40 may operate differently from each other. Hereinafter, the first air cleaner 20 and the second air cleaner 40 will be described sequentially.

Referring to FIG. 6, as described above, the first air cleaner 20 includes a first cleaner body 21, a first air cleaner cover 22, a first fan module 24, a first filter module 25, and a battery 26.

The first cleaner body 21 may include a first protrusion 210. The first protrusion 210 may protrude from one surface of the first cleaner body 21. In this embodiment, the first protrusion 210 may be disposed on a side of the first cleaner body 21. When the first cleaner body 21 is coupled to the first fixing unit 13, the first protrusion 210 may perform a function of a stopper fixed to the first fixing unit 13.

The first cleaner body 21 may include a first duct 211. The first duct 211 may protrude from the first protrusion 210. The first duct 211 may protrude further from the first protrusion 210. The first duct 211 may be disposed inside the first protrusion 210.

The first duct 211 may be inserted into the first fixing part 13 of the mask body 10. The first duct 211 may connect the first cleaner body 21 to the mask body 10. The first duct 211 may be understood as a passage for supplying the air filtered by the first air cleaner 20 to the mask body 10.

When the first duct 211 is inserted into the first fixing part 13, and the first protrusion 210 contacts the first fixing part 13, the first air cleaner 20 may be fixed to the mask body 10. When the first duct 211 is separated from the first fixing part 13, the first air cleaner 20 and the mask body 10 may be separated from each other.

A first air flow hole 211a may be defined in the first duct 211 and the first protrusion 210. The first air flow hole 211a may be defined by opening the inside of the first duct 211 and the first protrusion 210. The first air flow hole 211a may pass through the first duct 211 and the first protrusion 210.

One side of the first air flow hole 211a may communicate with a first air flow space 214 defined in the first cleaner body 21. The other side of the first air flow hole 211a may communicate with a first passage 124a of the mask body 10.

The first cleaner body 21 may include a first fixing hook 212. The first fixing hook 212 may be disposed on the first duct 211. When the first duct 211 is inserted into the first fixing part 13, the first fixing hook 212 may be hooked to be fixed to the first fixing part 13.

An installation hole for installing the first fixing hook 212 may be disposed at one side of the first duct 211. The first fixing hook 212 is disposed in the installation hole, and when the first duct 211 is inserted into the first fixing part 13, the first fixing hook 212 may be selectively hooked to be fixed to the first fixing part 13.

The mask device 1 may include a first wire tube 213. The first wire tube 213 may protrude from the first cleaner body 21. In this embodiment, the first wire tube 213 may protrude from a side surface of the first cleaner body 21. Also, the first wire tube 213 may be disposed at one side of the first duct 211.

The first wire tube 213 may be understood as a passage through which the electric wire 19 (see FIG. 8) passes. Also, the first wire tube 213 may be inserted into a first wire tube insertion hole (not shown) of the first fixing part 13. The first wire tube 213 may be connected to a first accommodation space 215 defined in the first cleaner body 21.

The first wire tube 213 may include a first wire through-hole 213a. The first wire through-hole 213a may be defined by opening the inside of the first wire tube 213. One side of the first wire through-hole 213a may communicate with the first accommodation space 215.

In this embodiment, the other side of the first wire through-hole 213a may communicate with a third passage 124c of the mask body 10. A portion of the air passing through the third passage 124c may be introduced into the first accommodation space 215 by the first wire through-hole 213a. When air in the third passage 124c flows into the first accommodation space 215, a plurality of components stored in the first accommodation space 215 may be cooled.

The first cleaner body 21 may include a first partition rib 216. The first partition rib 216 may be provided inside the first cleaner body 21. The first partition rib 216 may partition the internal space of the first cleaner body 21 into the first air flow space 214 and the first accommodation space 215.

An inner surface of the first cleaner body 21 may protrude to provide the first partition rib 216. In this embodiment, the first partition rib 216 may be disposed to correspond to the first fan module 24 and the first filter module 25 mounted in the first air flow space 214. The battery 26 may be disposed in the first accommodation space 215. That is, the first partition rib 216 may partition the internal space of the first cleaner body 21 into a space in which the air passes and a space in which the electric components are disposed.

The air forced by the first fan module 24 and filtered by the first filter module 25 may flow to the first passage 124a through the first air flow hole 211a. The first fan module 24 may include a fan and a motor, and the second filter module 45 may include various filters.

The first cleaner body 21 may include a first hook 217. The first hook 217 may be provided in plurality. The first hook 217 may allow the first ear hook part 30 and the first cleaner body 21 to be coupled to each other.

The first hook 217 may be disposed on the side surface of the first cleaner body 21. The first hook 217 may protrude outward from the side surface of the first cleaner body 21. Also, a portion of the first hook 217 protruding outward may be bent in a direction different from the protruding direction. In this embodiment, a plurality of first hooks 217 may be provided at both side surfaces of the first cleaner body 21.

The first cleaner body 21 may include a first opening 219. The first opening 219 may be understood as an opening through which the first departure prevention strap 281 of the first departure prevention part 28 passes. The first opening 219 may be defined in a size corresponding to the first departure prevention strap 281.

In this embodiment, the first opening 219 may be defined in the other side of the first protrusion 210. The first opening 219 may be spaced apart from the first wire tube 213. That is, the first protrusion 210 may be disposed between the first opening 219 and the first wire tube 213.

The first cleaner cover 22 may be detachably mounted on the opened upper surface of the first cleaner body 21. When the first cleaner cover 22 is mounted on the first cleaner body 21, the internal space of the first cleaner body 21 may be partitioned into the first air flow space 214 and the first accommodation space 215. The first cleaner body 21 and the first cleaner cover 22 may be coupled to each other in a fitting manner or a coupling manner.

The first cleaner cover 22 may include a first suction hole 221. The first suction hole 221 may be defined in a portion of the first cleaner cover 22 that covers the first air flow space 214. That is, air passing through the plurality of first suction holes 221 may be suctioned into the first air flow space 214. The first suction hole 221 may be defined with a plurality of openings or may have a mesh shape.

The first cleaner cover 22 may include a first switch 222. For example, the first switch 222 may be provided as a power switch that turns on/off the first air cleaner 20. Also, the first switch 222 may be used as a manipulation switch for controlling the operation of the first air cleaner 20 according to the duration, the number of times of pressing the first switch 222, and the like. When provided as the manipulation switch, the first switch 222 may include a first power switch for turning on/off the power and a plurality of manipulation switches for controlling the operation.

Referring to FIG. 7, the second air cleaner 40 includes a second cleaner body 41, a second air cleaner cover 42, a second fan module 44, a second filter module 45, and a circuit board 46.

The second cleaner body 41 may include a second protrusion 410. The second protrusion 410 may protrude from one surface of the second cleaner body 41. In this embodiment, the second protrusion 410 may be disposed on a side surface of the second cleaner body 41. When the second cleaner body 41 is coupled to the second fixing part 14, the second protrusion 410 may perform a function of a stopper fixed to the second fixing part 14.

The second cleaner body 41 may include a second duct 411. The second duct 411 may protrude from the second protrusion 410. The second duct 411 may further protrude from the second protrusion 410. The second duct 411 may be disposed inside the second protrusion 410.

The second duct 411 may be inserted into the second fixing part 14 of the mask body 10. The second duct 411 may connect the second cleaner body 41 to the mask body 10. The second duct 411 may be understood as a passage for supplying the air filtered by the second air cleaner 40 to the mask body 10.

When the second duct 411 is inserted into the second fixing part 14, and the second protrusion 410 contacts the second fixing part 14, the second air cleaner 40 may be fixed to the mask body 10. When the second duct 411 is separated from the second fixing part 14, the second air cleaner 40 and the mask body 10 may be separated from each other.

A second air flow hole 411a may be defined in the second duct 411 and the second protrusion 410. The second air flow hole 411a may be defined by opening the inside of the second duct 411 and the second protrusion 410. The second air flow hole 411a may pass through the second duct 411 and the second protrusion 410.

One side of the second air flow hole 411a may communicate the second air flow space 414 defined in the second cleaner body 41. The other side of the second air flow hole 411a may communicate with the second passage 124b of the mask body 10.

The second cleaner body 41 may include a second fixing hook 412. The second fixing hook 412 may be disposed on the second duct 411. When the second duct 411 is inserted into the second fixing part 14, the second fixing hook 412 may be fixed to the second fixing part 14.

An installation hole for installing the second fixing hook 412 may be defined in one side of the second duct 411. The second fixing hook 412 is disposed in the installation hole, and when the second duct 411 is inserted into the second fixing part 14, the second fixing hook 412 may be selectively fixed to the second fixing part 14.

The mask device 1 may include a second wire tube 413. The second wire tube 413 may protrude from the second cleaner body 41. In this embodiment, the second wire tube 413 may protrude from a side surface of the second cleaner body 41. Also, the second wire tube 413 may be disposed at one side of the second duct 411.

The second wire tube 413 may be understood as a passage through which the wire 19 (see FIG. 8) passes. Also, the second wire tube 413 may be inserted into a second wire tube insertion hole 142 (see FIG. 8) of the second fixing part 14. The second wire tube 413 may be connected to a second accommodation space 415 defined in the second cleaner body 41.

The second wire tube 413 may include a second wire through-hole 413a. The second wire through-hole 413a may be defined by opening the inside of the second wire tube 413. One side of the second wire through-hole 413a may communicate with the second accommodation space 415.

In this embodiment, the other side of the second wire through-hole 413a may communicate with the third passage 124c of the mask body 10. A portion of the air passing through the third passage 124c may be introduced into the second accommodation space 415 through the second wire through-hole 413a. When air in the third passage 124c is introduced into the second accommodation space 415, a plurality of components stored in the second accommodation space 415 may be cooled.

The second cleaner body 41 may include a second partition rib 416. The second partition rib 416 may be provided inside the second cleaner body 41. The second partition rib 416 may partition the internal space of the second cleaner body 41 into a second air flow space 414 and a second accommodation space 415.

An inner surface of the second cleaner body 41 may protrude to provide the second partition rib 416. In this embodiment, the second partition rib 416 may be disposed to correspond to the second fan module 44 and the second filter module 45 mounted in the second air flow space 414. The circuit board 46 may be disposed in the second accommodation space 415. That is, the second partition rib 416 may partition the internal space of the second cleaner body 41 into a space in which the air passes and a space in which the electric components are disposed.

The air forced by the second fan module 44 and filtered by the second filter module 45 may flow to the second passage 124b through the second air flow hole 411a. The second fan module 44 may include a fan and a motor, and the second filter module 45 may include various filters.

The circuit board 46 may control an operation of one or more of the first air cleaner 20 and the second air cleaner 40. The circuit board 46 may include a control unit, a communication unit, an information storage unit, and the like. When an operation signal is inputted from one or more of the first switch 222 and the second switch 422, the circuit board 46 may generate a control signal so that one or more of the first air cleaner 20 and the second air cleaner 40 operate.

One or more of the first air cleaner 20 and the second air cleaner 40 may operate by the control signal. The circuit board 46 may be connected to one or more of the first air cleaner 20 and the second air cleaner 40 by the wire 19 (see FIG. 8). The circuit board 46 may transmit and receive power and control signals through the wire 19.

The second cleaner body 41 may include a second hook 417. The second hook 417 may be provided in plurality. The second hook 417 may allow the second ear hook part 50 and the second cleaner body 41 to be coupled to each other.

The second hook 417 may be disposed on a side surface of the second cleaner body 41. The second hook 417 may protrude outward from the side surface of the second cleaner body 41. Also, a portion of the second hook 417 protruding outward may be bent in a direction different from the protruding direction. In this embodiment, a plurality of second hooks 417 may be provided at both side surfaces of the second cleaner body 41.

The second cleaner body 41 may include a second opening 419. The second opening 419 may be understood as an opening through which the second departure prevention strap 481 (see FIG. 8) of the second departure prevention part 48 passes. The second opening 419 may have a size corresponding to that of the second separation prevention strap 481.

In this embodiment, the second opening 419 may be defined in the other side of the second protrusion 410. The second opening 419 may be defined to be spaced apart from the second wire tube 413. That is, the second protrusion 410 may be disposed between the second opening 419 and the second wire tube 413.

The second cleaner cover 42 may be detachably mounted on an opened top surface of the second cleaner body 41. When the second cleaner cover 42 is mounted on the second cleaner body 41, the internal space of the second cleaner body 41 may be partitioned into the second air flow space 414 and the second accommodation space 415. The second cleaner body 41 and the second cleaner cover 42 may be coupled in a fitting manner or a coupling manner.

The second cleaner cover 42 may include a second suction hole 421. The second suction hole 421 may be defined in a portion of the second cleaner cover 42 covering the second air flow space 414. That is, air passing through the plurality of second suction holes 421 may be suctioned into the second air flow space 414. The second suction hole 421 may be provided with a plurality of openings or may have a mesh shape.

The second cleaner cover 42 may include a second switch 422. For example, the second switch 422 may be provided as a power switch that turns on/off the second air cleaner 40. Also, the second switch 422 may be used as a manipulation switch for controlling the operation of the second air cleaner 40 according to the duration, the number of times of pressing the second switch 422, and the like. When provided as the manipulation switch, the second switch 422 may include a second power switch for turning on/off the power and a plurality of manipulation switches for controlling the operation.

FIG. 8 is a view illustrating a state in which the mask device is folded according to an embodiment.

As illustrated in FIG. 8, in the mask device 1 according to the present invention, the first air cleaner 20 and the second air cleaner 40 may be folded with respect to the mask body 10.

Also, as illustrated in FIGS. 1 to 3, the first air cleaner 20 and the second air cleaner 40 may be fixed to both sides of the mask body 10. The user may wear the mask device 1 in a state in which the first air cleaner 20 and the second air cleaner 40 are fixed to both sides of the mask body 10.

In detail, the first and second fixing parts 13 and 14 of the mask body 10 may include the first and second duct insertion holes 141 and the first and second wire tube insertion holes 142, respectively. When the first and second air cleaners 20 and 40 are fixed to the first and second fixing parts 13 and 14, respectively, the first and second air cleaners 20 may be respectively inserted into the first and second air cleaners 141, and the first and second wire tubes 213 and 413 may be respectively inserted into the first and second wire tube insertion holes 132. Also, the first and second fixing hooks 212 and 412 of the first and second air cleaners 20 and 40 may be hooked to be fixed to the first and second fixing parts 13 and 14.

On the other hand, when the user does not use the mask device 1, the first air cleaner 20 and the second air cleaner 40 may be folded with respect to the mask body 10. When the first air cleaner 20 and the second air cleaner 40 are folded toward the frame 11 of the mask body 10, an area of the frame 11 of the mask body 10, which is exposed to the external space, may be minimized by the first air cleaner 20 and the second air cleaner 40. That is, it may prevent the frame 11 disposed adjacent to the user's nose and mouth from being contaminated by being exposed to the external space.

In detail, the hooking of the first and second fixing hooks 212 and 412 hooked to be fixed to the first and second fixing parts 13 and 14 may be released. When the hooking of the first and second fixing hooks 212 and 412 are released, the first and second cleaner bodies 21 and 41 may be separated from the first and second fixing parts 13 and 14. Here, the first and second fixing parts 13 and 14 and the first and second cleaner bodies 21 and 41 may be connected to each other by the first and second departure prevention parts 28 and 48.

That is, when the first and second fixing parts 13 and 14 and the first and second cleaner bodies 21 and 41 are separated, the first and second cleaner bodies 21 and 41 may be prevented from being separated from the first and second fixing parts 13 and 14 by the first and second departure prevention parts 28 and 48. Also, the first and second cleaner bodies 21 and 41 may rotate toward the frame 11 of the mask body 10 by the first and second departure prevention straps 281 and 481 of the first and second departure prevention parts 28 and 48.

In this embodiment, the first air cleaner 20 and the second air cleaner 40 are folded toward the mask body 10 by the first and second departure prevention parts 28 and 48. However, a hinge may be provided between the first air cleaner 20 and the first fixing part 13. Also, a hinge may be provided between the second air cleaner 40 and the second fixing part 14.

Also, in this embodiment, in the state where the first ear hook part 30 and the second ear hook part 50 are mounted to the first air cleaner 20 and the second air cleaner 40, the first air cleaner 20 and the second air cleaner 40 are folded with respect to the mask body 10. However, in the state in which the first ear hook part 30 and the second ear hook part 50 are separated from the first air cleaner 20 and the second air cleaner 40, the first air cleaner 20 and the second air cleaner 40 may be folded with respect to the mask body 10.

Hereinafter, a flow of air through this configuration will be described. FIG. 9 is a view illustrating a flow of air flowing by the mask device according to an embodiment. FIG. 9 illustrates a flow of air when the mask device 1 operates in a state in which the mask device 1 covers the user's nose and mouth.

In a state where the mask device 1 is contacts the face of the user, the user may turn on/off one or more of the first switch 222 and the second switch 422 to drive the mask device 1.

*190 When the mask device 1 operates, the first fan module 24 of the first air cleaner 20 and the second fan module 44 of the second air cleaner 40 operate to suction the external air. When the first fan module 24 and the second fan module 44 operate, the first suction hole 221 of the first air cleaner 20 and the second suction hole of the second air cleaner 40 may suction the external air. A flow direction of the external air introduced through the first suction hole 221 and the second suction hole 421 is indicated by reference symbol A.

The external air suctioned into the first suction hole 221 and the second suction hole 421 may be filtered by the first filter module 25 and the second filter module 45. The filtered air may be introduced into the inflow hole 111 of the mask body 10 after passing through the first passage 124a and the second passage 124b of the mask body 10.

A flow direction of the air passing through the first passage 124a and the second passage 124b and then discharged to the inflow hole 111 is indicated by reference symbol B. The air introduced into the inflow hole 111 may be supplied to the user's nose and mouth, the user may inhale the filtered air. Also, the user may breathe smoothly because the air is forced to flow by the first fan module 24 and the second fan module 44.

The user may inhale the filtered air after exhaling the filtered air. The air exhaled from the user's nose and mouth may be introduced into the outflow hole 112 of the mask body 10. The air exhaled because the air is continuously supplied through the inflow hole 111 may flow toward the outflow hole 112. The air introduced into the outflow hole 112 may flow into the third passage 124c of the mask body 10. Here, a flow direction of air exhaled from the user's nose and mouth is indicated by reference symbol C.

The air introduced into the third passage 124c may pass through the third passage 124c. The air passing through the third passage 124c may be discharged to the discharge hole 128 of the mask body 10. The discharge hole 128 may discharge the air flowing through the third passage 124c into the external space. A flow direction of air discharged from the third passage 124c through the discharge hole 128 and into the external space is indicated by reference symbol D.

FIG. 10 is a view illustrating a configuration for controlling the mask device according to an embodiment.

As illustrated in FIG. 10, the mask device 1 according to an embodiment is provided with a control unit 46 for controlling each configuration. Here, the control unit 46 may correspond to the circuit board described above. Thus, the same reference numerals are used, and their descriptions will be cited.

However, this is merely an example, and the control unit 46 may be provided separately from the circuit board. Also, the control unit 46 may be provided outside the mask device 1. For example, the control unit 46 may perform only a function of transmitting a control command inputted from a user terminal.

The control unit 46 may control the first fan module 24 and the second fan module 44 by the first switch 222 and the second switch 422. Particularly, it may be understood that the first switch 222 and the second switch 422 transmit an ON/OFF signal of the mask device 1 to the control unit 46. This control is quoted above.

Also, the mask device 1 according to an embodiment includes a breathing measurement sensor 60 for detecting a breathing quantity of the user. The breathing measurement sensor 60 may include a variety of sensors that is capable of detecting the user's breathing quantity. Particularly, the breathing measurement sensor 60 may be installed at a side of the outflow hole 112 to measure characteristics of the air discharged by the user.

For example, the breathing measurement sensor 60 may correspond to a flow rate sensor for measuring a flow rate of air C flowing through the third passage 124c. Also, the flow rate of the air passing through the outflow hole 112 or the discharge hole 128 may be measured. Accordingly, the flow rate of the air discharged by the user may be measured.

Also, the breathing measurement sensor 60 may correspond to a differential pressure sensor for measuring a pressure of the air C flowing through the third passage 124c. Also, the pressure of the air passing through the outflow hole 112 or the discharge hole 128 may be measured. Thus, the user may measure a pressure of the discharged air.

Also. the breathing measurement sensor 60 may correspond to a vibration detection sensor for detecting predetermined vibration. Particularly, the vibration detection sensor may be installed to detect vibration of the check valve installed in the outflow hole 112 or the discharge hole 128.

As described above, the breathing measurement sensor 60 may measure the characteristics of the air discharged by the user. Also, the mask device 1 includes a memory unit 70 that stores data relating to the relationship between the characteristic measured in the breathing measurement sensor 60 and the breathing quantity. Such data may be created and stored through experimentation.

Thus, the control unit 46 may determine the user's breathing quantity by using the breathing measurement sensor 60 and the memory unit 70. Approximatively, the control unit 46 may determine that the quantity of user's breathing increases when the flow rate increases. Also, the control unit 46 may determine that the user's breathing quantity increases when the pressure or vibration increases.

Also, the control unit 46 determines that the user's breathing quantity increases, the first fan module 24 and the second fan module increase in RPM. That is, the first fan module 24 and the second fan module 44 rotate at a higher speed to supply more air.

Based on this control configuration, the control flow in an exemplary situation will be described.

FIG. 11 is a flowchart illustrating a method for controlling the mask device according to an embodiment.

As illustrated in FIG. 11, a mask device 1 is turned on (S10). Here, the turn-on of the mask device 1 means that an ON signal is transmitted to the control unit 46 through a first switch 222 or a second switch 224.

Also, when the mask device 1 is turned on (S10), a first fan module 24 and a second fan module 44 operates at A rpm (S20). That is, when the mask device 1 is turned on regardless of the user's breathing quantity, the first fan module 24 and the second fan module 44 rotate at a predetermined speed to allow air to flow.

Here, the value A may be understood as a predetermined base rpm value. The value A may be set based on when a user generally breathes. For example, the value A may be set to an rpm corresponding to 9 L/min corresponding to an average breathing quantity when the user walks.

Also, the user's breathing quantity is measured, and it is determined whether the measured breathing quantity exceeds a predetermined reference breathing quantity (hereinafter, referred to as a first reference breathing quantity) (S30). For example, the first reference breathing quantity may correspond to an average breathing quantity when the user moves at a faster speed than normal walking.

That is, when the user moves at the faster speed than the walking, the breathing quantity may exceed the first reference breathing quantity. Also, when the user moves by working or stops, the breathing quantity may be equal to or less than the first reference breathing quantity.

When the measured breathing quantity is less than or equal to the first reference breathing quantity, the first fan module 24 and the second fan module 44 continue to operate at A rpm. On the other hand, when the measured breathing quantity exceeds the first reference breathing quantity, the first fan module 24 and the second fan module 44 are operated at B rpm (S40).

Here, the value B corresponds to an rpm value greater than the value A (B>A). For example, the value B may be set to an rpm corresponding to 20 L/min corresponding to an average breathing quantity when the user walks fast.

Also, the user's breathing quantity is measured, and it is determined whether the measured breathing quantity exceeds a predetermined reference breathing quantity (hereinafter, referred to as a second reference breathing quantity) (S50). For example, the first reference breathing quantity may correspond to an average breathing quantity when the user moves at a faster speed than fast walking.

That is, when the user moves at the faster speed than the fast walking, the breathing quantity may exceed the first reference breathing quantity. Also, when the user moves at a slower speed than the fast walking, the breathing quantity may be less than or equal to the second reference breathing quantity.

When the measured breathing quantity is less than or equal to the second reference breathing quantity, the first fan module 24 and the second fan module 44 continue to operate at B rpm. On the other hand, when the measured breathing quantity exceeds the second reference breathing quantity, the first fan module 24 and the second fan module 44 operate at C rpm (S60).

Here, the value C corresponds to an rpm value greater than value B (C>B>A). For example, the value C may be set to an rpm corresponding to 40 L/min corresponding to an average breathing quantity when the user moves and runs.

Also, when the mask device 1 is turned off (S70), the first fan module 24 and the second fan module 44 are stopped.

Such the control is illustrative and not limited thereto. For example, the first fan module 24 and the second fan module 44 may operate at various rpm by being divided into more various processes. Also, a linear graph of the measured breath quantity and rpm may be created to operate according thereto.

Also, numerical values for the first and second reference breaths are provided as examples for convenience of description. Thus, breathing quantity may be measured on a more diverse basis and stored as a reference quantity.

As described above, if the user's breathing quantity increases as the user moves at a higher speed, the air may be supplied correspondingly. Thus, the user may not feel discomfort in breathing even when the user wears the mask device 1 and performs various activities. In addition, as the user's discomfort is removed, the wearing time may increase to more effectively protect the user's bronchial tube.

FIG. 12 is a view of a mask device according to another embodiment.

As illustrated in FIG. 12, the mask device 1 includes an exhaust fan module 80. Here, the mask device 1 illustrated in FIG. 12 corresponds to a form in which only the exhaust fan module 80 is added to the mask device illustrated in FIGS. 1 to 9. Thus, all descriptions of FIGS. 1 to 9 are cited, and the same reference numerals are used.

The exhaust fan module 80 is installed to allow air discharged by the user to flow. That, unlike the first fan module 24 and the second fan module 44 installed at the suction-side, the exhaust fan module 80 is installed at a discharge-side. Here, the first fan module 24 and the second fan module 44 are referred to as a first suction fan module 24 and a second suction fan module 44 so as to be distinguished from the exhaust fan module 80.

Also, the first suction fan module 24 and the second suction fan module 44 may correspond to a main fan module for suctioning external air to flow. The exhaust fan module 80 may be understood as an auxiliary fan module installed to allow the user to breathe more smoothly. Thus, the exhaust fan module 80 may be provided in lower performance and a smaller quantity than those of each of the first suction fan module 24 and the second suction fan module 44.

The exhaust fan module 80 may be installed in a mask body 10. Particularly, the exhaust fan module 80 may be installed in a third passage 124*c*. That is, the exhaust fan module 80 is disposed between a frame 11 and a front cover 12.

In addition, the exhaust fan module 80 may be disposed at a center side of a third passage 124*c*. Also, the exhaust fan module 80 is disposed between a pair of outflow holes 112. Also, it may be understood that the exhaust fan module 80 is disposed between a pair of discharge holes 128.

FIG. 13 is a view illustrating a configuration for controlling the mask device according to another embodiment.

As illustrated in FIG. 13, the mask device 1 according to an embodiment is provided with a control unit 46 for controlling each configuration. Here, the control unit 46 may correspond to the circuit board described above. Thus, the same reference numerals are used, and their descriptions will be cited.

However, this is merely an example, and the control unit 46 may be provided separately from the circuit board. Also, the control unit 46 may be provided outside the mask device 1. For example, the control unit 46 may perform only a function of transmitting a control command inputted from a user terminal.

The control unit 46 may control the first fan module 24 and the second fan module 44 by the first switch 222 and the second switch 422. This control is quoted above.

Also, the control unit 46 may control the exhaust fan module 80. The exhaust fan module 80 may be controlled to correspond to the first fan module 24 and the second fan module 44. That is, the exhaust fan module 80, the first fan module 24, and the second fan module 44 may be controlled to balance the suction and exhaust amounts so that the user breathes comfortably.

Here, the exhaust fan module 80, the first fan module 24, and the second fan module 44 may be controlled according to the user's breathing quantity. Particularly, the user's breathing quantity may be measured by a load applied to the exhaust fan module 80. For example, the user's breathing quantity may be measured by changing power consumption (Vsp signal) of the exhaust fan module 80.

The control unit 46 may determine that the user's breathing quantity increases when the load of the exhaust fan module 80 increases. Also, the control unit 46 determines that the user's breathing quantity increases, the first fan module 24 and the second fan module increase in RPM. That is, the first fan module 24 and the second fan module 44 rotate at a higher speed to supply more air.

Based on this control configuration, the control flow in an exemplary situation will be described.

FIG. 14 is a flowchart illustrating a method for controlling the mask device according to another embodiment.

As illustrated in FIG. 14, when the mask device 1 is turned on (S100), the first fan module 24, the second fan module 44 and the exhaust fan module 80 operate (S110). Here, the first fan module 24, the second fan module 44, and the exhaust fan module 80 may increase in rpm to a predetermined rising rate.

Also, the first fan module 24, the second fan module 44 and the exhaust fan module 80 operate at the same time, and simultaneously, a load of the exhaust fan module 80 is measured (S110). That is, the exhaust fan module 80 operate, and the load may be measured immediately.

Also, it is determined whether the load (hereinafter, referred to as a measured load) measured by the exhaust fan module 80 is less than or equal to a pre-stored reference load (S120). Here, the reference load may correspond to a load applied to the exhaust fan module 80 when the user breathes comfortably. Thus, the reference load may correspond to a specific numerical range.

When the measured load exceeds the reference load, it is determined as a high load state and continues to increase in rpm (S125). Also, subsequently, the load may be measured and compared to the reference load, and rpm may increases until the reference load is lower than the reference load. Here, rpm of the first fan module 24, the second fan module 44, and the exhaust fan module 80 may be changed at different rates.

Also, when the measured load is less than the reference load, it is determined whether or not the reference load or more (S130). When the measured load is less than the reference load, it is determined as a low load state to reduce rpm (S135). Also, if the measured load is greater than or equal to the reference load and less than or equal to the reference load, that is, rpm is maintained (S140).

Also, when the mask device 1 is turned off (S150), the first fan module 24, the second fan module 44, and the exhaust fan module 80 are stopped.

In summary, when the user breathes comfortably, the load is determined as the reference load, and when the load is higher than the reference load, rpm increases to maintain the user's breathing smoothly. Also, if the load is lower than the reference load, rpm may be lowered to protect the fan module and increase its lifespan.

This is exemplary control and not limited thereto. For example, as in the control (an embodiment) described in FIG. 11, a plurality of reference loads may be stored, and rpm may be raised in stages. Also, the mask device according to the first embodiment may also be controlled by determining the reference breath volume range to increase or decreases in rpm.

Also, the mask device 1 may be provided with both the exhaust fan module 80 and the breathing measurement sensor 60. The user's breathing quantity may be more accurately measured by using the load of the exhaust fan module 80 and the characteristics of the discharged air detected in the breathing measurement sensor 60.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

The invention claimed is:

1. A mask device comprising:
   a mask body to cover a nose and a mouth of a user;
   a first air cleaner to filter a first air;
   a second air cleaner to filter a second air;
   a first passage, a second passage, and a third passage, which are partitioned from each other within the mask body;
   a first suction fan disposed at the first air cleaner to suction the first air so that the first air flows to the first passage;
   a second suction fan disposed at the second air cleaner to suction the second air so that the second air flows to the second passage;
   an exhaust fan disposed at the third passage;
   a control unit configured to determine a breathing quantity of the user based on a load of the exhaust fan and to control an RPM of each of the first suction fan, the second suction fan, and the exhaust fan; and
   wherein, when the load of the exhaust fan increases, the control unit is configured to control the first suction fan, the second suction fan, and the exhaust fan so that the RPM of each of the first suction fan, the second suction fan, and the exhaust fan increases.

2. The mask device according to claim 1, further comprising a switch to be switched on or off,
   wherein the control unit is configured to control the first suction fan, the second suction fan, and the exhaust fan so that each of the first suction fan, the second suction fan, and the exhaust fan operates or does not operate based on whether the switch is switched on or off, respectively.

3. The mask device according to claim 2, wherein,
   when the load of the exhaust fan is greater than a reference load, the control unit is configured to control the RPM of each of the first suction fan, the second suction fan, and the exhaust fan to increase.

4. The mask device according to claim 1, comprising a breathing measurement sensor to detect the breathing quantity of the user,
   wherein the breathing measurement sensor comprises one of a flow sensor to measure a flow of air flowing through the third passage, a differential pressure sensor to measure a pressure of the air flowing through the third passage, or a vibration detection sensor to detect a vibration of a check valve disposed at the third passage.

5. The mask device according to claim 1, wherein the mask body comprises:
   an inflow hole communicating with the first passage and the second passage so that the first air filtered by the first air cleaner and the second air filtered by the second air cleaner are supplied to the user; and
   an outflow hole communicating with the third passage so that a discharged air from the user is discharged to the third passage.

6. The mask device according to claim 5, wherein the third passage is disposed below the first passage and the second passage so that the inflow hole is disposed at a portion corresponding to the nose of the user, and the outflow hole is disposed at a portion corresponding to the mouth of the user.

7. The mask device according to claim 5, wherein the mask body comprises a discharge hole to discharge the discharged air introduced into the third passage to an outside of the mask device.

8. The mask device according to claim 7, wherein a first suction hole through which the first air is suctioned is defined at the first air cleaner, and
a second suction hole through which the second air is suctioned is defined at the second air cleaner.

9. The mask device according to claim 8, wherein the first air cleaner comprises a first filter disposed between the first suction hole and the first suction fan to filter foreign substances from the first air,
and the second air cleaner comprises a second filter disposed between the second suction hole and the second suction fan to filter foreign substances from the second air.

10. The mask device according to claim 1, wherein the mask body comprises:
a frame to be disposed in front of the nose and the mouth of the user and in which an inflow hole through which the filtered first and second air pass and an outflow hole through which a discharged air from the user passes are defined; and
a front cover to define an outer appearance of the mask body, the front cover being coupled to the frame to provide the first passage, the second passage, and the third passage.

11. The mask device according to claim 10, wherein the exhaust fan is disposed between the frame and the front cover.

12. A mask device, comprising:
a memory;
a control unit coupled to the memory, the control unit configured to:
drive a first suction fan, a second suction fan, and an exhaust fan;
filter a first air by driving the first suction fan and filter a second air by driving the second suction fan, wherein the filtered first and second air flow to a mask body configured to cover a nose and a mouth of a user so as to be supplied to the user;
discharge discharged air from the user to an outside of the mask device by driving the exhaust fan;
and
change an RPM of each of the first suction fan, the second suction fan, and the exhaust fan according to a load of the exhaust fan.

13. The mask device according to claim 12, wherein the control unit is configured to drive the exhaust fan so as to measure the load of the exhaust fan, and
when the measured load is greater than a reference load, the control unit is configured to increase an RPM of each of the first suction fan, the second suction fan, and the exhaust fan.

14. The mask device according to claim 13, wherein, when the measured load is less than the reference load, the control unit is configured to decrease the RPM of each of the first suction fan, the second suction fan, and the exhaust fan.

15. The mask device according to claim 13, wherein, when the measured load is equal to the reference load, the control unit is configured to maintain the RPM of each of the first suction fan, the second suction fan, and the exhaust fan.

16. The mask device according to claim 12, wherein the changes in the RPM of each of the first suction fan, the second suction fan, and the exhaust fan are different from each other.

17. The mask device according to claim 12, wherein the control unit is configured to use one of a flow rate, a pressure, or a vibration of the discharge air from the user for the change in the RPM of each of the first suction fan, the second suction fan, and the exhaust fan.

18. The mask device according to claim 12, wherein, when the mask device is turned on, the control unit is configured to drive each of the first suction fan, the second suction fan, and the exhaust fan at a preset RPM.

* * * * *